(12) United States Patent
Kawai et al.

(10) Patent No.: US 7,328,125 B2
(45) Date of Patent: Feb. 5, 2008

(54) MEASURING METHOD OF CYLINDRICAL BODY

(75) Inventors: Yasuhiro Kawai, Susono (JP); Kyoichi Teramoto, Toride (JP); Yoichi Kawamorita, Abiko (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 11/469,094

(22) Filed: Aug. 31, 2006

(65) Prior Publication Data

US 2007/0100554 A1    May 3, 2007

Related U.S. Application Data

(63) Continuation-in-part of application No. PCT/JP2006/304200, filed on Feb. 28, 2006, and a continuation-in-part of application No. 11/281,603, filed on Nov. 18, 2005, now abandoned, which is a continuation of application No. PCT/JP2005/016470, filed on Sep. 1, 2005.

(30) Foreign Application Priority Data

| Sep. 1, 2004 | (JP) | 2004-254363 |
|---|---|---|
| Sep. 2, 2005 | (JP) | 2005-254327 |
| Feb. 28, 2006 | (JP) | 2006-052880 |

(51) Int. Cl.
*G01B 7/00* (2006.01)
*G01B 15/00* (2006.01)

(52) U.S. Cl. ................................................ 702/155
(58) Field of Classification Search ............... 702/155
See application file for complete search history.

(56) References Cited

U.S. PATENT DOCUMENTS

| 5,325,134 A * | 6/1994 | Kohayakawa ............... 351/212 |
| 6,674,523 B2 * | 1/2004 | Kawamorita et al. ..... 356/237.2 |
| 7,212,883 B2 * | 5/2007 | Hollingshead et al. ...... 700/182 |
| 2004/0098221 A1 * | 5/2004 | Katamachi .................. 702/157 |
| 2006/0052977 A1 * | 3/2006 | Wilson ........................ 702/155 |

FOREIGN PATENT DOCUMENTS

| JP | 4-148819 | 5/1992 |
| JP | 6-147879 | 5/1994 |
| JP | 6-201375 | 7/1994 |
| JP | 8-005341 | 1/1996 |
| JP | 2000-249540 | 9/2000 |
| WO | WO 2006/025603 | 3/2006 |

* cited by examiner

*Primary Examiner*—Michael Nghiem
(74) *Attorney, Agent, or Firm*—Fitzpatrick, Cella, Harper & Scinto

(57) ABSTRACT

A measuring method of a shape of a cross-sectional circle which is orthogonal to an axis of a cylinder includes steps of calculating distances between a reference point and points on a circumference on the basis of change of the distances of at least three predetermined points on the circumference of the cross-sectional circle to the reference point set in the cross-sectional circle by the rotation of the cylinder, and specifying the shape of the cross-sectional circle.

12 Claims, 24 Drawing Sheets

FIG. 10

| SAMPLE 1 | S0 | S45 | S90 | Δx | Δy | TRUE VALUE | X COOR- DINATE | Y COOR- DINATE | X COORDI- NATE OF CENTER | Y COORDI- NATE OF CENTER |
|---|---|---|---|---|---|---|---|---|---|---|
| 0 | 83.936 | 83.901 | 83.909 | | | | 0.000 | 83.936 | -0.058 | -0.041 |
| 45 | 83.920 | 83.908 | 83.927 | 0.026 | -0.066 | 83.986 | -59.387 | 59.387 | | |
| 90 | 83.911 | 83.911 | 83.933 | -0.003 | -0.102 | 84.013 | -84.013 | 0.000 | | |
| 135 | 83.932 | 83.888 | 83.917 | -0.069 | -0.109 | 84.041 | -59.426 | -59.426 | | |
| 180 | 83.935 | 83.913 | 83.911 | -0.102 | -0.078 | 84.013 | 0.000 | -84.013 | | |
| 225 | 83.923 | 83.911 | 83.930 | -0.111 | -0.034 | 83.957 | 59.366 | -59.366 | | |
| 270 | 83.930 | 83.910 | 83.926 | -0.087 | 0.021 | 83.909 | 83.909 | 0.000 | | |
| 315 | 83.930 | 83.915 | 83.923 | -0.034 | 0.042 | 83.888 | 59.317 | 59.317 | | |

| SAMPLE 2 | S0 | S45 | S90 | Δx | Δy | TRUE VALUE | X COOR- DINATE | Y COOR- DINATE | X COORDI- NATE OF CENTER | Y COORDI- NATE OF CENTER |
|---|---|---|---|---|---|---|---|---|---|---|
| 0 | 83.926 | 83.914 | 83.943 | | | | 0.000 | 83.926 | -0.031 | -0.037 |
| 45 | 83.944 | 83.915 | 83.924 | 0.010 | -0.026 | 83.970 | -59.375 | 59.375 | | |
| 90 | 83.954 | 83.919 | 83.916 | -0.010 | -0.061 | 84.015 | -84.015 | 0.000 | | |
| 135 | 83.933 | 83.925 | 83.934 | -0.036 | -0.092 | 84.025 | -59.415 | -59.415 | | |
| 180 | 83.926 | 83.918 | 83.943 | -0.072 | -0.079 | 84.005 | 0.000 | -84.005 | | |
| 225 | 83.943 | 83.909 | 83.923 | -0.102 | -0.034 | 83.977 | 59.381 | -59.381 | | |
| 270 | 83.940 | 83.910 | 83.920 | -0.085 | -0.009 | 83.949 | 83.949 | 0.000 | | |
| 315 | 83.939 | 83.908 | 83.918 | -0.059 | 0.001 | 83.938 | 59.353 | 59.353 | | |

| SAMPLE 3 | S0 | S45 | S90 | Δx | Δy | TRUE VALUE | X COOR- DINATE | Y COOR- DINATE | X COORDI- NATE OF CENTER | Y COORDI- NATE OF CENTER |
|---|---|---|---|---|---|---|---|---|---|---|
| 0 | 83.924 | 83.926 | 83.935 | | | | 0.000 | 83.924 | -0.013 | -0.038 |
| 45 | 83.929 | 83.922 | 83.935 | 0.009 | -0.012 | 83.941 | -59.355 | 59.355 | | |
| 90 | 83.909 | 83.923 | 83.952 | 0.028 | -0.053 | 83.962 | -83.962 | 0.000 | | |
| 135 | 83.908 | 83.926 | 83.955 | 0.014 | -0.065 | 83.973 | -59.378 | -59.378 | | |
| 180 | 83.925 | 83.907 | 83.936 | -0.026 | -0.068 | 83.993 | 0.000 | -83.993 | | |
| 225 | 83.925 | 83.928 | 83.936 | -0.037 | -0.054 | 83.979 | 59.382 | -59.382 | | |
| 270 | 83.920 | 83.925 | 83.936 | -0.057 | -0.020 | 83.940 | 83.940 | 0.000 | | |
| 315 | 83.919 | 83.923 | 83.930 | -0.049 | 0.025 | 83.894 | 59.322 | 59.322 | | |

| SAMPLE 4 | S0 | S45 | S90 | Δx | Δy | TRUE VALUE | X COOR- DINATE | Y COOR- DINATE | X COORDI- NATE OF CENTER | Y COORDI- NATE OF CENTER |
|---|---|---|---|---|---|---|---|---|---|---|
| 0 | 83.915 | 83.893 | 83.915 | | | | 0.000 | 83.915 | -0.039 | -0.037 |
| 45 | 83.927 | 83.899 | 83.905 | 0.012 | -0.035 | 83.962 | -59.370 | 59.370 | | |
| 90 | 83.923 | 83.901 | 83.907 | -0.008 | -0.078 | 84.001 | -84.001 | 0.000 | | |
| 135 | 83.911 | 83.900 | 83.919 | -0.043 | -0.100 | 84.011 | -59.405 | -59.405 | | |
| 180 | 83.915 | 83.897 | 83.916 | -0.085 | -0.076 | 83.991 | 0.000 | -83.991 | | |
| 225 | 83.927 | 83.894 | 83.905 | -0.106 | -0.032 | 83.959 | 59.368 | -59.368 | | |
| 270 | 83.925 | 83.899 | 83.904 | -0.087 | 0.003 | 83.922 | 83.922 | 0.000 | | |
| 315 | 83.924 | 83.895 | 83.901 | -0.058 | 0.019 | 83.905 | 59.330 | 59.330 | | |

| SAMPLE 5 | S0 | S45 | S90 | Δx | Δy | TRUE VALUE | X COOR- DINATE | Y COOR- DINATE | X COORDI- NATE OF CENTER | Y COORDI- NATE OF CENTER |
|---|---|---|---|---|---|---|---|---|---|---|
| 0 | 83.931 | 83.905 | 83.920 | | | | 0.000 | 83.931 | -0.097 | -0.063 |
| 45 | 83.945 | 83.886 | 83.907 | 0.002 | -0.066 | 84.011 | -59.404 | 59.404 | | |
| 90 | 83.942 | 83.905 | 83.909 | -0.022 | -0.127 | 84.069 | -84.069 | 0.000 | | |
| 135 | 83.930 | 83.907 | 83.924 | -0.087 | -0.143 | 84.073 | -59.449 | -59.449 | | |
| 180 | 83.930 | 83.883 | 83.921 | -0.148 | -0.120 | 84.050 | 0.000 | -84.050 | | |
| 225 | 83.926 | 83.906 | 83.908 | -0.185 | -0.039 | 83.965 | 59.372 | -59.372 | | |
| 270 | 83.923 | 83.905 | 83.920 | -0.130 | 0.045 | 83.878 | 83.878 | 0.000 | | |
| 315 | 83.922 | 83.904 | 83.923 | -0.042 | 0.079 | 83.843 | 59.286 | 59.286 | | |

FIG. 11

| SAMPLE 6 | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 83.929 | 83.920 | 83.928 | | | | 0.000 | 83.929 | -0.034 | -0.021 |
| 45 | 83.935 | 83.914 | 83.923 | 0.003 | -0.024 | 83.959 | -59.368 | 59.368 | | |
| 90 | 83.938 | 83.925 | 83.920 | -0.009 | -0.039 | 83.977 | -83.977 | 0.000 | | |
| 135 | 83.932 | 83.918 | 83.924 | -0.035 | -0.049 | 83.981 | -59.383 | -59.383 | | |
| 180 | 83.928 | 83.918 | 83.928 | -0.049 | -0.039 | 83.967 | 0.000 | -83.967 | | |
| 225 | 83.934 | 83.920 | 83.922 | -0.059 | -0.008 | 83.942 | 59.356 | -59.356 | | |
| 270 | 83.930 | 83.926 | 83.926 | -0.041 | 0.018 | 83.912 | 83.912 | 0.000 | | |
| 315 | 83.934 | 83.921 | 83.921 | -0.021 | 0.035 | 83.899 | 59.326 | 59.326 | | |

| SAMPLE 7 | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 83.942 | 83.912 | 83.924 | | | | 0.000 | 83.942 | -0.046 | -0.038 |
| 45 | 83.926 | 83.925 | 83.930 | 0.018 | -0.042 | 83.968 | -59.374 | 59.374 | | |
| 90 | 83.925 | 83.909 | 83.941 | -0.001 | -0.082 | 84.007 | -84.007 | 0.000 | | |
| 135 | 83.930 | 83.912 | 83.927 | -0.041 | -0.094 | 84.024 | -59.414 | -59.414 | | |
| 180 | 83.941 | 83.920 | 83.925 | -0.062 | -0.065 | 84.006 | 0.000 | -84.006 | | |
| 225 | 83.926 | 83.912 | 83.928 | -0.096 | -0.036 | 83.962 | 59.370 | -59.370 | | |
| 270 | 83.920 | 83.910 | 83.930 | -0.076 | -0.002 | 83.918 | 83.918 | 0.000 | | |
| 315 | 83.927 | 83.915 | 83.926 | -0.036 | 0.031 | 83.896 | 59.323 | 59.323 | | |

| SAMPLE 8 | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 83.913 | 83.899 | 83.922 | | | | 0.000 | 83.913 | -0.037 | -0.040 |
| 45 | 83.918 | 83.901 | 83.918 | 0.019 | -0.036 | 83.954 | -59.364 | 59.364 | | |
| 90 | 83.924 | 83.903 | 83.912 | -0.001 | -0.071 | 83.995 | -83.995 | 0.000 | | |
| 135 | 83.919 | 83.902 | 83.916 | -0.038 | -0.094 | 84.013 | -59.406 | -59.406 | | |
| 180 | 83.913 | 83.906 | 83.923 | -0.072 | -0.079 | 83.992 | 0.000 | -83.992 | | |
| 225 | 83.919 | 83.898 | 83.919 | -0.094 | -0.039 | 83.958 | 59.367 | -59.367 | | |
| 270 | 83.918 | 83.901 | 83.915 | -0.077 | -0.004 | 83.922 | 83.922 | 0.000 | | |
| 315 | 83.917 | 83.903 | 83.917 | -0.041 | 0.014 | 83.903 | 59.328 | 59.328 | | |

| SAMPLE 9 | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 83.945 | 83.920 | 83.915 | | | | 0.000 | 83.945 | -0.040 | -0.029 |
| 45 | 83.943 | 83.923 | 83.921 | 0.001 | -0.032 | 83.975 | -59.379 | 59.379 | | |
| 90 | 83.919 | 83.912 | 83.939 | -0.008 | -0.083 | 84.002 | -84.002 | 0.000 | | |
| 135 | 83.926 | 83.920 | 83.937 | -0.038 | -0.078 | 84.004 | -59.400 | -59.400 | | |
| 180 | 83.946 | 83.904 | 83.913 | -0.089 | -0.052 | 83.998 | 0.000 | -83.998 | | |
| 225 | 83.940 | 83.922 | 83.921 | -0.083 | -0.025 | 83.965 | 59.372 | -59.372 | | |
| 270 | 83.935 | 83.920 | 83.920 | -0.078 | 0.015 | 83.920 | 83.920 | 0.000 | | |
| 315 | 83.941 | 83.919 | 83.926 | -0.039 | 0.037 | 83.904 | 59.329 | 59.329 | | |

| SAMPLE 10 | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 83.922 | 83.901 | 83.910 | | | | 0.000 | 83.922 | -0.057 | -0.043 |
| 45 | 83.915 | 83.896 | 83.919 | 0.018 | -0.055 | 83.970 | -59.376 | 59.376 | | |
| 90 | 83.916 | 83.901 | 83.920 | -0.002 | -0.095 | 84.011 | -84.011 | 0.000 | | |
| 135 | 83.924 | 83.894 | 83.911 | -0.059 | -0.107 | 84.031 | -59.419 | -59.419 | | |
| 180 | 83.921 | 83.899 | 83.911 | -0.100 | -0.086 | 84.007 | 0.000 | -84.007 | | |
| 225 | 83.915 | 83.903 | 83.919 | -0.112 | -0.036 | 83.951 | 59.362 | -59.362 | | |
| 270 | 83.918 | 83.900 | 83.918 | -0.089 | 0.018 | 83.900 | 83.900 | 0.000 | | |
| 315 | 83.920 | 83.899 | 83.916 | -0.035 | 0.033 | 83.887 | 59.317 | 59.317 | | |

FIG. 12

| SAMPLE 1 | X | Y | DISTANCE | | MAX | MIN |
|---|---|---|---|---|---|---|
| 0 | 0.058 | 83.977 | 83.977 | | 83.977 | 83.955 |
| 45 | 59.328 | 59.428 | 83.974 | | | |
| 90 | 83.955 | 0.041 | 83.955 | | | |
| 135 | 59.368 | 59.385 | 83.970 | | | |
| 180 | 0.058 | 83.972 | 83.972 | | | |
| 225 | 59.425 | 59.325 | 83.969 | | | |
| 270 | 83.967 | 0.041 | 83.967 | | | |
| 315 | 59.376 | 59.359 | 83.958 | | | |

| SAMPLE 2 | X | Y | DISTANCE | | MAX | MIN |
|---|---|---|---|---|---|---|
| 0 | 0.031 | 83.963 | 83.963 | | 83.986 | 83.963 |
| 45 | 59.345 | 59.412 | 83.974 | | | |
| 90 | 83.985 | 0.037 | 83.985 | | | |
| 135 | 59.384 | 59.378 | 83.978 | | | |
| 180 | 0.031 | 83.969 | 83.969 | | | |
| 225 | 59.411 | 59.344 | 83.973 | | | |
| 270 | 83.980 | 0.037 | 83.980 | | | |
| 315 | 59.384 | 59.390 | 83.986 | | | |

| SAMPLE 3 | X | Y | DISTANCE | | MAX | MIN |
|---|---|---|---|---|---|---|
| 0 | 0.013 | 83.962 | 83.962 | | 83.962 | 83.930 |
| 45 | 59.342 | 59.393 | 83.959 | | | |
| 90 | 83.949 | 0.038 | 83.949 | | | |
| 135 | 59.365 | 59.340 | 83.937 | | | |
| 180 | 0.013 | 83.955 | 83.955 | | | |
| 225 | 59.395 | 59.344 | 83.961 | | | |
| 270 | 83.953 | 0.038 | 83.953 | | | |
| 315 | 59.335 | 59.360 | 83.930 | | | |

| SAMPLE 4 | X | Y | DISTANCE | | MAX | MIN |
|---|---|---|---|---|---|---|
| 0 | 0.039 | 83.952 | 83.952 | | 83.962 | 83.952 |
| 45 | 59.331 | 59.407 | 83.961 | | | |
| 90 | 83.962 | 0.037 | 83.962 | | | |
| 135 | 59.366 | 59.367 | 83.957 | | | |
| 180 | 0.039 | 83.954 | 83.954 | | | |
| 225 | 59.407 | 59.330 | 83.960 | | | |
| 270 | 83.961 | 0.037 | 83.961 | | | |
| 315 | 59.369 | 59.367 | 83.959 | | | |

| SAMPLE 5 | X | Y | DISTANCE | | MAX | MIN |
|---|---|---|---|---|---|---|
| 0 | 0.097 | 83.994 | 83.994 | | 83.994 | 83.955 |
| 45 | 59.308 | 59.467 | 83.987 | | | |
| 90 | 83.973 | 0.063 | 83.973 | | | |
| 135 | 59.352 | 59.386 | 83.960 | | | |
| 180 | 0.097 | 83.988 | 83.988 | | | |
| 225 | 59.469 | 59.310 | 83.989 | | | |
| 270 | 83.974 | 0.063 | 83.974 | | | |
| 315 | 59.382 | 59.348 | 83.955 | | | |

FIG. 13

| SAMPLE 6 | X | Y | DISTANCE | | MAX | MIN |
|---|---|---|---|---|---|---|
| 0 | 0.034 | 83.950 | 83.950 | | 83.951 | 83.938 |
| 45 | 59.334 | 59.389 | 83.950 | | | |
| 90 | 83.944 | 0.021 | 83.944 | | | |
| 135 | 59.350 | 59.362 | 83.942 | | | |
| 180 | 0.034 | 83.946 | 83.946 | | | |
| 225 | 59.390 | 59.335 | 83.951 | | | |
| 270 | 83.945 | 0.021 | 83.945 | | | |
| 315 | 59.360 | 59.347 | 83.938 | | | |

| SAMPLE 7 | X | Y | DISTANCE | | MAX | MIN |
|---|---|---|---|---|---|---|
| 0 | 0.046 | 83.980 | 83.980 | | 83.980 | 83.955 |
| 45 | 59.328 | 59.412 | 83.962 | | | |
| 90 | 83.962 | 0.038 | 83.962 | | | |
| 135 | 59.368 | 59.376 | 83.965 | | | |
| 180 | 0.046 | 83.968 | 83.968 | | | |
| 225 | 59.416 | 59.333 | 83.968 | | | |
| 270 | 83.964 | 0.038 | 83.964 | | | |
| 315 | 59.369 | 59.361 | 83.955 | | | |

| SAMPLE 8 | X | Y | DISTANCE | | MAX | MIN |
|---|---|---|---|---|---|---|
| 0 | 0.037 | 83.953 | 83.953 | | 83.959 | 83.952 |
| 45 | 59.327 | 59.404 | 83.956 | | | |
| 90 | 83.958 | 0.040 | 83.958 | | | |
| 135 | 59.369 | 59.366 | 83.958 | | | |
| 180 | 0.037 | 83.952 | 83.952 | | | |
| 225 | 59.404 | 59.327 | 83.956 | | | |
| 270 | 83.959 | 0.040 | 83.959 | | | |
| 315 | 59.365 | 59.368 | 83.957 | | | |

| SAMPLE 9 | X | Y | DISTANCE | | MAX | MIN |
|---|---|---|---|---|---|---|
| 0 | 0.040 | 83.974 | 83.974 | | 83.974 | 83.953 |
| 45 | 59.339 | 59.409 | 83.968 | | | |
| 90 | 83.962 | 0.029 | 83.962 | | | |
| 135 | 59.360 | 59.371 | 83.955 | | | |
| 180 | 0.040 | 83.969 | 83.969 | | | |
| 225 | 59.412 | 59.343 | 83.973 | | | |
| 270 | 83.960 | 0.029 | 83.960 | | | |
| 315 | 59.369 | 59.358 | 83.953 | | | |

| SAMPLE 10 | X | Y | DISTANCE | | MAX | MIN |
|---|---|---|---|---|---|---|
| 0 | 0.057 | 83.965 | 83.965 | | 83.965 | 83.955 |
| 45 | 59.319 | 59.419 | 83.961 | | | |
| 90 | 83.955 | 0.043 | 83.955 | | | |
| 135 | 59.362 | 59.375 | 83.960 | | | |
| 180 | 0.057 | 83.964 | 83.964 | | | |
| 225 | 59.419 | 59.319 | 83.960 | | | |
| 270 | 83.957 | 0.043 | 83.957 | | | |
| 315 | 59.374 | 59.361 | 83.958 | | | |

| SAMPLE No. | ROUNDNESS MEASURING INSTRUMENT RA-H5000AH | PRESENT MEASURING METHOD | DIFFERENCE |
|---|---|---|---|
| 1 | 21.9 | 22.2 | 0.3 |
| 2 | 22.1 | 23.3 | 1.2 |
| 3 | 31.1 | 32.3 | 1.2 |
| 4 | 8.8 | 9.5 | 0.7 |
| 5 | 38.0 | 38.3 | 0.3 |
| 6 | 11.3 | 13.1 | 1.8 |
| 7 | 23.6 | 25.0 | 1.4 |
| 8 | 6.8 | 6.9 | 0.1 |
| 9 | 19.4 | 21.6 | 2.2 |
| 10 | 9.3 | 10.8 | 1.5 |

UNIT : μm

FIG. 16

| SAMPLE No. | BY ROUNDNESS MEASURING INSTRUMENT RA-H5000AH | | BY PRESENT MEASURING METHOD | DIFFERENCE |
|---|---|---|---|---|
| | CENTERING AND LEVELING | MEASURED VALUE | | |
| 1 | 55 | 23 | 35 | 43 |
| 2 | 54 | 23 | 35 | 42 |
| 3 | 55 | 23 | 35 | 43 |
| 4 | 54 | 23 | 35 | 42 |
| 5 | 54 | 23 | 35 | 42 |
| 6 | 54 | 23 | 35 | 42 |
| 7 | 55 | 23 | 35 | 43 |
| 8 | 54 | 23 | 35 | 42 |
| 9 | 54 | 23 | 35 | 42 |
| 10 | 54 | 23 | 35 | 42 |
| AVERAGE | 54.3 | 23.0 | 35.0 | 42.3 |
| TOTAL | 543 | 230 | 350 | 423 |

UNIT : SECONDS

FIG. 18

|  | 0° | 15° | 30° | 45° | 60° | 75° | 90° | 105° | 120° | 135° | 150° | 165° | 180° | 195° | 210° | 225° | 240° | 255° | 270° | 285° | 300° | 315° | 330° | 345° |
|---|---|---|---|---|---|---|---|---|---|---|---|---|---|---|---|---|---|---|---|---|---|---|---|---|
| S0 | 463.0 | 462.8 | 462.0 | 463.5 | 465.0 | 466.4 | 467.8 | 468.2 | 468.4 | 467.4 | 466.5 | 466.7 | 465.3 | 465.3 | 464.7 | 464.3 | 464.3 | 465.6 | 467.3 | 469.2 | 470.6 | 469.6 | 467.0 | 464.4 |
| S15 | 462.2 | 462.9 | 463.9 | 466.5 | 468.1 | 469.7 | 470.2 | 469.4 | 468.3 | 466.1 | 464.7 | 464.4 | 463.7 | 465.3 | 467.0 | 466.1 | 467.6 | 468.9 | 469.5 | 470.4 | 470.3 | 467.4 | 464.6 | 462.3 |
| S60 | 461.8 | 464.4 | 467.5 | 470.4 | 472.0 | 473.2 | 471.9 | 468.5 | 464.0 | 459.7 | 458.4 | 459.1 | 461.1 | 465.2 | 469.2 | 471.2 | 472.5 | 471.8 | 469.5 | 466.9 | 462.9 | 460.2 | 458.7 | 459.7 |
| S75 | 463.4 | 465.7 | 468.8 | 471.3 | 472.8 | 473.8 | 472.0 | 468.3 | 463.4 | 459.5 | 459.5 | 459.2 | 462.6 | 466.7 | 470.6 | 472.7 | 473.4 | 471.6 | 468.6 | 465.7 | 462.1 | 460.2 | 460.0 | 461.6 |

FIG. 19

|  | 0° | 15° | 30° | 45° | 60° | 75° | 90° | 105° | 120° | 135° | 150° | 165° | 180° | 195° | 210° | 225° | 240° | 255° | 270° | 285° | 300° | 315° | 330° | 345° |
|---|---|---|---|---|---|---|---|---|---|---|---|---|---|---|---|---|---|---|---|---|---|---|---|---|
| S0 | 0.0 | -0.2 | -1.0 | 0.5 | 2.0 | 3.4 | 4.8 | 5.2 | 5.4 | 4.4 | 3.5 | 3.7 | 2.3 | 2.5 | 1.7 | 1.3 | 1.3 | 2.6 | 4.3 | 6.2 | 7.6 | 6.2 | 4.0 | 1.4 |
| S15 | -0.8 | -0.1 | 0.9 | 3.5 | 5.1 | 6.7 | 7.2 | 6.4 | 5.3 | 3.1 | 1.7 | 1.4 | 0.7 | 2.3 | 4.0 | 3.1 | 4.6 | 5.9 | 6.5 | 7.4 | 7.3 | 4.4 | 1.6 | -0.7 |
| S60 | -1.2 | 1.4 | 4.5 | 7.4 | 9.0 | 10.2 | 8.9 | 5.5 | 1.0 | -3.3 | -4.6 | -3.9 | -1.8 | 2.2 | 6.2 | 8.2 | 9.5 | 8.8 | 6.5 | 3.9 | -0.1 | -2.8 | -4.3 | -3.3 |
| S75 | 0.4 | 2.7 | 5.8 | 8.3 | 9.8 | 10.8 | 9.0 | 5.3 | 0.4 | -3.5 | -3.5 | -3.8 | -0.4 | 3.7 | 7.6 | 9.4 | 10.4 | 8.6 | 5.6 | 2.7 | -0.9 | -2.8 | -3.0 | -1.4 |

|  | 0° | 15° | 30° | 45° | 60° | 75° | 90° | 105° | 120° | 135° | 150° | 165° | 180° | 195° | 210° | 225° | 240° | 255° | 270° | 285° | 300° | 315° | 330° | 345° |
|---|---|---|---|---|---|---|---|---|---|---|---|---|---|---|---|---|---|---|---|---|---|---|---|---|
| S0 | 50.0 | 50.2 | 51.0 | 49.5 | 48.0 | 46.6 | 45.2 | 44.8 | 44.6 | 45.6 | 46.5 | 46.3 | 47.7 | 47.5 | 48.3 | 48.7 | 48.7 | 47.4 | 45.7 | 43.8 | 42.4 | 43.8 | 46.0 | 48.6 |
| S15 | 50.8 | 50.1 | 49.1 | 46.5 | 44.9 | 43.3 | 42.8 | 43.6 | 44.7 | 46.9 | 48.3 | 48.6 | 49.3 | 47.7 | 46.0 | 46.9 | 45.4 | 44.1 | 43.5 | 42.6 | 42.7 | 45.6 | 48.4 | 50.7 |
| S60 | 51.2 | 48.6 | 45.5 | 42.6 | 41.0 | 39.8 | 41.1 | 44.5 | 49.0 | 53.3 | 54.6 | 53.9 | 51.8 | 47.8 | 43.8 | 41.8 | 40.5 | 41.2 | 43.5 | 46.1 | 50.1 | 52.8 | 54.3 | 53.3 |
| S75 | 49.6 | 47.3 | 44.2 | 41.7 | 40.2 | 39.2 | 41.0 | 44.7 | 49.6 | 53.5 | 53.5 | 53.8 | 50.4 | 46.3 | 42.4 | 40.6 | 39.6 | 41.4 | 44.4 | 47.3 | 50.9 | 52.8 | 53.0 | 51.4 |

FIG. 20

|  | S0 | S15 | S60 | S75 | Δx | Δy | TRUE VALUE |
|---|---|---|---|---|---|---|---|
| 0° | 50.0 | 50.8 | 51.2 | 49.6 |  |  |  |
| 15° | 50.2 | 50.1 | 48.6 | 47.3 | -4.4 | 1.3 | 48.9 |
| 30° | 51.0 | 49.1 | 45.5 | 44.2 | -5.8 | 1.7 | 49.3 |
| 45° | 49.5 | 46.5 | 42.6 | 41.7 | -4.5 | -1.6 | 51.1 |
| 60° | 48.0 | 44.9 | 41.0 | 40.2 | -10.0 | -3.8 | 51.8 |
| 75° | 46.6 | 43.3 | 39.8 | 39.2 | -9.5 | -6.3 | 52.9 |
| 90° | 45.2 | 42.8 | 41.1 | 41.0 | -5.8 | -8.8 | 54.0 |
| 105° | 44.8 | 43.6 | 44.5 | 44.7 | -2.0 | -10.3 | 55.1 |
| 120° | 44.6 | 44.7 | 49.0 | 49.6 | 1.4 | -11.1 | 55.7 |
| 135° | 45.6 | 46.9 | 53.3 | 53.5 | 4.5 | -10.3 | 55.9 |
| 150° | 46.5 | 48.3 | 54.6 | 53.5 | 3.0 | -8.7 | 55.2 |
| 165° | 46.3 | 48.6 | 53.9 | 53.8 | 1.7 | -7.3 | 53.6 |
| 180° | 47.7 | 49.3 | 51.8 | 50.4 | -3.9 | -3.4 | 51.1 |
| 195° | 47.5 | 47.7 | 47.8 | 46.3 | -9.5 | -1.0 | 48.5 |
| 210° | 48.3 | 46.0 | 43.8 | 42.4 | -14.4 | 1.3 | 47.0 |
| 225° | 48.7 | 46.9 | 41.8 | 40.6 | -16.3 | 4.2 | 44.5 |
| 240° | 48.7 | 45.4 | 40.5 | 39.6 | -15.9 | 5.2 | 43.5 |
| 255° | 47.4 | 44.1 | 41.2 | 41.4 | -11.0 | 3.6 | 43.8 |
| 270° | 45.7 | 43.5 | 43.5 | 44.4 | -4.5 | 0.9 | 44.8 |
| 285° | 43.8 | 42.6 | 46.1 | 47.3 | 1.0 | -2.5 | 46.3 |
| 300° | 42.4 | 42.7 | 50.1 | 50.9 | 8.3 | -6.0 | 48.4 |
| 315° | 43.8 | 45.6 | 52.8 | 52.8 | 11.2 | -5.9 | 49.7 |
| 330° | 46.0 | 48.4 | 54.3 | 53.0 | 10.7 | -4.2 | 50.2 |
| 345° | 48.6 | 50.7 | 53.3 | 51.4 | 7.2 | -1.4 | 50.0 |

FIG. 21

| MEASUREMENT ANGLE (°) | MEASURED VALUE (μm) | X COOR-DINATE | Y COOR-DINATE |
|---|---|---|---|
| 0 | 50.0 | 0.0 | 50.0 |
| 15 | 48.9 | -12.7 | 47.3 |
| 30 | 49.3 | -24.6 | 42.7 |
| 45 | 51.1 | -36.2 | 36.2 |
| 60 | 51.8 | -44.9 | 25.9 |
| 75 | 52.9 | -51.1 | 13.7 |
| 90 | 54.0 | -54.0 | 0.0 |
| 105 | 55.1 | -53.2 | -14.3 |
| 120 | 55.7 | -48.3 | -27.9 |
| 135 | 55.9 | -39.6 | -39.6 |
| 150 | 55.2 | -27.6 | -47.8 |
| 165 | 53.6 | -13.9 | -51.8 |
| 180 | 51.1 | 0.0 | -51.1 |
| 195 | 48.5 | 12.5 | -46.8 |
| 210 | 47.0 | 23.5 | -40.7 |
| 225 | 44.5 | 31.4 | -31.4 |
| 240 | 43.5 | 37.6 | -21.7 |
| 255 | 43.8 | 42.3 | -11.3 |
| 270 | 44.8 | 44.8 | 0.0 |
| 285 | 46.3 | 44.8 | 12.0 |
| 300 | 48.4 | 41.9 | 24.2 |
| 315 | 49.7 | 35.1 | 35.1 |
| 330 | 50.2 | 25.1 | 43.5 |
| 345 | 50.0 | 12.9 | 48.3 |

| X | Y | DISTANCE |
|---|---|---|
| 4.5 | 50.5 | 50.7 |
| 8.2 | 47.7 | 48.4 |
| 20.1 | 43.1 | 47.6 |
| 31.7 | 36.6 | 48.4 |
| 40.4 | 26.4 | 48.2 |
| 46.6 | 14.2 | 48.7 |
| 49.6 | 0.5 | 49.6 |
| 48.7 | 13.8 | 50.6 |
| 43.8 | 27.4 | 51.6 |
| 35.1 | 39.1 | 52.5 |
| 23.1 | 47.4 | 52.7 |
| 9.4 | 51.3 | 52.2 |
| 4.5 | 50.6 | 50.8 |
| 17.0 | 46.4 | 49.4 |
| 28.0 | 40.3 | 49.0 |
| 35.9 | 31.0 | 47.4 |
| 42.1 | 21.3 | 47.2 |
| 46.8 | 10.9 | 48.0 |
| 49.3 | 0.5 | 49.3 |
| 49.3 | 12.5 | 50.8 |
| 46.4 | 24.7 | 52.5 |
| 39.6 | 35.6 | 53.3 |
| 29.6 | 43.9 | 53.0 |
| 17.4 | 48.8 | 51.8 |

| COORDINATES OF CENTER | X | -4.5 |
|---|---|---|
| | Y | -0.5 |

| ROUNDNESS | 6.1 |
|---|---|

FIG. 23

|  |  |  |  | DISTANCE TO $O_0$ | | |
|---|---|---|---|---|---|---|
| ROTATION (°) | ΔS0 | ΔS45 | ΔS90 | S0 | S45 | S90 |
| 0 | 0.479 | 0.322 | 0.340 | 41.969 | 41.951 | 41.956 |
| 45 | 0.486 | 0.318 | 0.331 | 41.962 | 41.955 | 41.965 |
| 90 | 0.492 | 0.316 | 0.328 | 41.957 | 41.957 | 41.968 |
| 135 | 0.481 | 0.328 | 0.337 | 41.967 | 41.945 | 41.959 |
| 180 | 0.480 | 0.316 | 0.339 | 41.698 | 41.958 | 41.957 |
| 225 | 0.485 | 0.317 | 0.330 | 41.963 | 41.956 | 41.966 |
| 270 | 0.482 | 0.317 | 0.332 | 41.966 | 41.957 | 41.964 |
| 315 | 0.482 | 0.314 | 0.334 | 41.966 | 41.959 | 41.963 |

FIG. 24

| | S0 | S45 | S90 | Δx | Δy | TRUE VALUE | X COOR-DINATE | Y COOR-DINATE | X COORDI-NATE OF CENTER | Y COORDI-NATE OF CENTER |
|---|---|---|---|---|---|---|---|---|---|---|
| 0 | 41.969 | 41.951 | 41.956 | | | | 0.000 | 41.969 | -0.029 | -0.021 |
| 45 | 41.962 | 41.955 | 41.965 | 0.014 | -0.033 | 41.994 | -29.694 | 29.694 | | |
| 90 | 41.957 | 41.957 | 41.968 | -0.001 | -0.051 | 42.008 | -42.008 | 0.000 | | |
| 135 | 41.967 | 41.945 | 41.959 | -0.035 | -0.054 | 42.021 | -29.713 | -29.713 | | |
| 180 | 41.968 | 41.958 | 41.957 | -0.051 | -0.039 | 42.007 | 0.000 | -42.007 | | |
| 225 | 41.963 | 41.956 | 41.966 | -0.055 | -0.016 | 41.979 | 29.684 | -29.684 | | |
| 270 | 41.966 | 41.957 | 41.964 | -0.043 | 0.010 | 41.956 | 41.956 | 0.000 | | |
| 315 | 41.966 | 41.959 | 41.963 | -0.017 | 0.022 | 41.944 | 29.659 | 29.659 | | |

FIG. 25

| | X | Y | DISTANCE |
|---|---|---|---|
| 0 | 0.029 | 41.989 | 41.989 |
| 45 | 29.665 | 29.715 | 41.988 |
| 90 | 41.979 | 0.021 | 41.979 |
| 135 | 29.684 | 29.693 | 41.986 |
| 180 | 0.029 | 41.986 | 41.986 |
| 225 | 29.713 | 29.663 | 41.986 |
| 270 | 41.985 | 0.021 | 41.985 |
| 315 | 29.688 | 29.680 | 41.979 |

| MAX | MIN |
|---|---|
| 41.989 | 41.979 |

| ROUNDNESS | 0.010 |
|---|---|

| | |
|---|---|
| 0°-180° | 83.975 |
| 90°-270° | 83.964 |

FIG. 28

| ANGLE(°) | 30mm | 35mm | 40mm | 60mm | 80mm | 90mm | 120mm | 140mm | 150mm | 180mm | 200mm | 210mm | 240mm | 260mm | 270mm | 300mm | 310mm | 320mm | 330mm | 350mm |
|---|---|---|---|---|---|---|---|---|---|---|---|---|---|---|---|---|---|---|---|---|
| 0° | 50.7 | 51.3 | 50.6 | 51.1 | 52.1 | 51.5 | 51.4 | 50.7 | 50.0 | 50.8 | 50.6 | 51.0 | 51.7 | 52.7 | 52.9 | 53.1 | 53.0 | 53.6 | 53.0 | 52.1 |
| 15° | 48.4 | 49.4 | 48.7 | 49.7 | 50.3 | 50.4 | 50.8 | 50.5 | 49.9 | 50.8 | 50.5 | 50.9 | 51.9 | 52.7 | 52.7 | 52.3 | 52.1 | 52.4 | 51.7 | 50.1 |
| 30° | 47.8 | 48.8 | 47.7 | 48.8 | 50.3 | 49.8 | 50.8 | 50.3 | 49.9 | 50.7 | 50.6 | 51.1 | 52.1 | 52.8 | 52.8 | 51.8 | 51.4 | 51.4 | 50.3 | 48.4 |
| 45° | 48.4 | 49.6 | 48.2 | 48.8 | 50.7 | 50.0 | 50.9 | 50.6 | 50.2 | 50.9 | 51.0 | 51.6 | 52.6 | 53.2 | 53.5 | 52.0 | 51.2 | 51.2 | 49.8 | 47.5 |
| 60° | 48.2 | 49.2 | 47.7 | 48.2 | 49.7 | 49.3 | 50.1 | 49.8 | 49.3 | 49.9 | 50.1 | 50.6 | 51.6 | 52.2 | 52.3 | 50.9 | 50.0 | 49.9 | 48.4 | 46.1 |
| 75° | 48.7 | 49.6 | 47.9 | 49.1 | 49.8 | 49.1 | 49.6 | 49.5 | 48.9 | 49.4 | 49.6 | 50.2 | 51.4 | 52.0 | 52.1 | 51.0 | 50.0 | 50.3 | 48.6 | 46.4 |
| 90° | 49.8 | 50.3 | 48.7 | 49.5 | 49.5 | 49.1 | 49.3 | 49.0 | 48.4 | 48.7 | 49.0 | 49.6 | 50.9 | 51.6 | 51.7 | 51.0 | 50.4 | 50.6 | 49.2 | 47.7 |
| 105° | 50.6 | 51.1 | 49.0 | 49.9 | 49.4 | 49.1 | 48.9 | 48.5 | 47.9 | 48.1 | 48.4 | 49.0 | 50.1 | 51.0 | 51.1 | 51.3 | 50.8 | 51.0 | 50.2 | 49.5 |
| 120° | 51.6 | 51.7 | 50.1 | 50.5 | 48.2 | 48.9 | 48.4 | 48.0 | 47.3 | 47.3 | 47.6 | 48.1 | 49.2 | 50.1 | 50.2 | 51.1 | 50.9 | 51.3 | 51.0 | 51.4 |
| 135° | 52.5 | 52.1 | 50.7 | 50.9 | 49.1 | 48.9 | 48.1 | 47.7 | 47.1 | 47.0 | 47.4 | 47.7 | 48.8 | 49.8 | 49.8 | 51.2 | 51.1 | 51.8 | 51.9 | 53.1 |
| 150° | 52.7 | 51.8 | 51.0 | 50.2 | 48.9 | 48.8 | 47.9 | 47.7 | 46.9 | 46.8 | 47.2 | 47.3 | 48.3 | 49.1 | 49.0 | 50.9 | 51.0 | 51.7 | 52.0 | 54.0 |
| 165° | 52.2 | 51.2 | 50.6 | 49.3 | 48.7 | 48.8 | 48.0 | 47.8 | 46.9 | 46.6 | 47.2 | 47.1 | 48.1 | 48.7 | 48.4 | 50.4 | 50.5 | 51.0 | 51.0 | 53.7 |
| 180° | 50.8 | 49.7 | 49.9 | 49.1 | 48.1 | 48.1 | 47.6 | 47.7 | 46.9 | 46.6 | 47.1 | 46.8 | 47.6 | 48.1 | 47.7 | 49.4 | 49.9 | 50.0 | 50.4 | 52.3 |
| 195° | 49.4 | 48.0 | 48.8 | 48.0 | 47.4 | 47.6 | 47.3 | 47.5 | 46.0 | 46.5 | 47.1 | 46.6 | 47.1 | 47.3 | 46.7 | 48.3 | 48.8 | 48.5 | 48.9 | 50.3 |
| 210° | 49.0 | 47.4 | 48.9 | 47.9 | 48.0 | 48.1 | 48.1 | 48.5 | 47.9 | 47.5 | 46.0 | 47.1 | 47.3 | 47.2 | 46.5 | 47.7 | 47.8 | 47.5 | 47.4 | 48.5 |
| 225° | 47.4 | 45.9 | 48.1 | 47.1 | 47.3 | 47.6 | 47.7 | 48.2 | 48.0 | 47.3 | 46.8 | 48.8 | 46.8 | 46.8 | 46.0 | 46.7 | 46.9 | 46.1 | 46.2 | 47.0 |
| 240° | 47.2 | 45.8 | 48.8 | 47.5 | 47.6 | 47.8 | 47.9 | 48.3 | 48.0 | 47.5 | 47.8 | 48.7 | 46.7 | 46.3 | 45.7 | 46.2 | 46.6 | 45.5 | 45.7 | 46.1 |
| 255° | 48.0 | 46.7 | 48.8 | 48.3 | 48.3 | 48.4 | 48.3 | 48.5 | 48.4 | 47.8 | 47.9 | 48.8 | 46.8 | 46.8 | 46.2 | 46.6 | 47.0 | 46.0 | 46.1 | 46.4 |
| 270° | 49.3 | 48.2 | 49.7 | 49.4 | 49.3 | 49.3 | 48.9 | 48.9 | 48.9 | 48.3 | 48.1 | 47.3 | 47.4 | 47.2 | 47.2 | 47.6 | 48.1 | 47.4 | 47.4 | 47.8 |
| 285° | 50.8 | 49.9 | 51.2 | 50.5 | 49.3 | 49.9 | 49.2 | 48.7 | 48.8 | 48.2 | 47.9 | 47.2 | 47.6 | 47.8 | 47.9 | 48.4 | 49.2 | 48.5 | 48.3 | 49.3 |
| 300° | 52.5 | 51.9 | 52.6 | 51.8 | 51.1 | 50.9 | 49.9 | 49.1 | 49.3 | 48.6 | 48.2 | 47.8 | 48.3 | 48.8 | 49.2 | 49.9 | 50.9 | 50.5 | 50.9 | 51.4 |
| 315° | 53.3 | 53.1 | 54.1 | 52.5 | 51.5 | 51.5 | 50.3 | 49.3 | 49.0 | 49.0 | 48.6 | 48.3 | 49.0 | 49.8 | 50.3 | 51.2 | 51.9 | 52.1 | 52.6 | 53.2 |
| 330° | 53.0 | 53.3 | 54.0 | 52.7 | 52.1 | 51.7 | 50.7 | 49.5 | 49.7 | 49.4 | 48.9 | 48.9 | 49.5 | 50.4 | 51.1 | 52.1 | 52.7 | 53.1 | 53.7 | 54.1 |
| 345° | 51.8 | 52.5 | 52.4 | 52.1 | 51.8 | 51.5 | 50.8 | 49.4 | 49.9 | 49.8 | 49.1 | 49.5 | 50.0 | 51.0 | 51.8 | 52.5 | 52.8 | 53.4 | 53.9 | 53.9 |

| MAX | MIN |
|---|---|
| 54.5 | 45.5 |

MEASURING METHOD OF CYLINDRICAL BODY

This application is a continuation-in-part application of International Application No. PCT/JP06/304200, filed Feb. 28, 2006, and is a continuation-in-part application of U.S. patent application Ser. No. 11/281,603 filed on Nov. 18, 2005, now abandoned which is a continuation of International Application No. PCT/JP05/016470 filed on Sep. 1, 2005, which claims the benefit of Japanese Patent Application No. 2004-254363 filed Sep. 1, 2004.

BACKGROUND OF THE INVENTION

1. Field of the Invention

The present invention relates to a measuring method of a shape of a cross-sectional circle in a direction orthogonal to an axis of a cylinder, and a shape of a cylinder, and a measuring method used for this. In particular, the present invention relates to the technology of contributing to precision measurement at the time of cutting an outer surface of a cylindrical member, as means of obtaining an accurate cylindrical member. The scopes of the measuring technique acquired by the present invention are various. In particular, the present inventor and et al. applied the present invention to an image forming member of an electrophotographic system of copier, laser beam printer, facsimile, or printer, or the measurement of its base substrate, and verified its effects.

2. Related Background Art

Heretofore, a cylindrical member whose shape is finished with predetermined accuracy has been used for an electrophotographic photosensitive drum or a development sleeve in an image forming apparatus such as an electrophotographic system of copier, laser beam printer, facsimile, or printing machine. An electrophotographic photosensitive drum is produced by giving a photosensitive film to a surface of a drum substrate which is finished with predetermined accuracy. Nevertheless, there is a problem that convexoconcave arises in a photosensitive film when the accuracy of dimensions of the drum substrate is low, and for this reason, a defect arises in an image of an image forming apparatus. Hence, in order to obtain high-precision image forming apparatus, high accuracy is required in a cylindricity, a roundness, and the like of the drum substrate.

Furthermore, also in the process of producing such a drum substrate, a highly precise measurement function aiming at assuring the accuracy of dimensions is required, and the following conventional technology is known as methods aiming at it. A method of measuring a surface shape by a zonal laser or other measuring means while standing and rotating a measured cylinder (a cylinder which is a measuring object, and this is the same hereafter) on a rotatable base (for example, refer to Japanese Patent Application Laid-Open No. H06-201375). A method of holding both ends of a measured cylinder with a certain holder and rotating the cylinder, and measuring the size of interrupting a zonal laser to measure cylindrical shape (for example, refer to Japanese Patent Application Laid-Open No. H08-005341). A method of performing measurement by the approximate calculation of the measured values acquired from displacement detectors facing an outer peripheral section of a measured cylinder by rotating the measured cylinder without fixing a rotation axis (for example, refer to Japanese Patent Application Laid-Open No. H06-147879) and the like. Nevertheless, in addition to such a request to extended-definition of an image forming apparatus, a simpler measuring system aiming at the reduction of manufacturing cost becomes indispensable in recent years. Furthermore, with mentioning a cylindrical measuring method with following needs as industrial product evaluation, items to be evaluated should be classified into the accuracy of dimensions as a cylinder, and partial geometrical defects of a surface, and measuring means suitable for each object should be used. Here, according to the measurement of accuracy of dimensions, in a field of measuring the accuracy of dimensions of a circumferential shape of a cylinder, especially a circumferential shape of a cylinder which premises that it has such a high level of accuracy that the present invention may make it an object, it is possible to make it sufficient evaluation even if the number of measured points is a small number comparatively when each measured value is very exact. Hence, industrially, it is preferable to reduce the number of measurement points as much as possible, and to aim at reducing processing time. On the other hand, even if the number of measurement points is increased at the time of evaluating a partial geometrical defect of a cylindrical surface, it is difficult to evaluate all microdefects such as a hairline-like scratch defect. Hence, it is not preferable also in this point to make the number of measurement points increase. Hence, evaluation means by surface defect analysis such as image processing which replaces it should be used. That is, when performing the dimensional accuracy measurement of a circumferential shape of a cylinder as industrial product evaluation, from a viewpoint of pursuing measurement efficiency, it can be said that it is most preferable that there are few loads concerning measurement, each measured value is exact, and the number of measurement points is suppressed to the minimum. In this point, although the conventional method of measuring a surface shape by measuring means such as a zonal laser while standing a measured cylinder on a rotatable base and rotating this (for example, refer to Japanese Patent Application Laid-Open No. H06-201375) can acquire very highly precise measured value, it is not easy to reduce measuring time and loads since preparatory work such as precise centering of the measured cylinder on the base in measurement is required. In addition, the method of holding both ends of a measured cylinder with a certain holder and rotating the cylinder, and measuring the size of interrupting a zonal laser to measure cylindrical shape (for example, refer to Japanese Patent Application Laid-Open No. H08-005341) can perform comparatively simple measurement. On the other hand, the variation of a cylindrical wall thickness affects a measured value, the fitting gap size of the holder of both ends, deformation of ends by a holding force, the vibration of a shaft arising at the time of rotating the measured cylinder, or the like becomes easily a cause of generating a measurement error. Furthermore, the method of performing measurement by the approximate calculation of the measured values acquired from displacement detectors facing an outer peripheral section of a measured cylinder by rotating the measured cylinder without fixing a rotation axis (for example, refer to Japanese Patent Application Laid-Open No. H06-147879) is simple and can suppress an influence of accuracy of an instrument concerning measurement over measurement result. On the other hand, this has a feature that, since the measurement result is approximately calculated values, it increases the accuracy of each measured value to make the number of measurement points and an order of an approximate calculation increase. It is required that the number of measurement points is at least 64 points or 100 points or more. Hence, it is hardly possible by this method to reduce the number of measurement points, and this method takes comparatively long measuring time.

Thus, the conventional technology has not provided a dimensional accuracy measuring method of a circumferential shape of a cylinder as industrial product evaluation which makes loads, concerning measurement, minimum from a viewpoint of measurement efficiency, and makes it possible for each measured value to be exact and to suppress the number of measurement points to the minimum.

SUMMARY OF THE INVENTION

In view of such problems, the present invention was conducted to aim at making loads of measurement few, making each measured value exact, and efficiently reducing the number of measurement points, in cylindrical dimension measurement, and in particular, the measurement of a circumferential shape.

That is, according to a first embodiment of the present invention, there is provided a measuring method of a shape of a cross-sectional circle which is orthogonal to an axis of a cylinder, characterized by comprising a step of calculating distances between a reference point and a circumference on the basis of the change of the distances of at least three predetermined points on the circumference of the cross-sectional circle to the reference point, which is set in the cross-sectional circle and is an intersection point of a rotation axis of a measured cylinder and the cross-sectional circle, by rotation of the cylinder, and specifying the shape of the cross-sectional circle.

Specifically, it is a measuring method of a shape of a cross-sectional circle, which is orthogonal to an axis of a cylinder to be measured, by the following steps (i) to (v) using measuring means constructed of (a) a cylinder support jig, and (b) a mount having first, second and third sensors for detecting displacements, which are located on a cross-section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the second sensor and the third sensor are θ°, comprising: (i) a step of measuring each of distances $\Delta L1$, $\Delta L2$ and $\Delta L3$ between each of the first, second and third sensors and intersecting points of lines connecting the respective sensors and the $O_0$ with a circumference of the cross-sectional circle of the cylinder to be measured, (ii) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, wherein LS1, LS2 and LS3 are distances between each of the first, second and third sensors and the $O_0$, (iii) a step of rotating the cylinder to be measured by θ° in a direction toward the second sensor from the first sensor, and repeating the steps (i) and (ii), (iv) a step of calculating a distance $\Delta O1$ between a floating point O', which is a point on the cross-sectional circle of the cylinder to be measured corresponding to the $O_0$ before the rotation in the step (iii), and a line passing through the $O_0$ and intersecting at right-angle with the line connecting the first sensor and the $O_0$, from L1 and L2 obtained in the step (ii) and L2 and L3 obtained in the step (iii), (v) a step of calculating a distance between the O' and a line intersecting at right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and $\Delta O1$ obtained in the step (iv).

Most of conventional measuring methods require loads so as to pursue the accuracy of mechanical limitation of a cylinder centers as a measurement reference position for the purpose of acquiring the higher accuracy of measurement. On the other hand, a method which the present invention provides premises that this cylinder center is such a virtual center that moves by rotation, i.e., a floating point (floating center). Therefore, the measuring method of the present invention is characterized by tracking, theoretically catching, and limiting a position of this floating point each time the measured cylinder rotates by one notch on the basis of the change of numerical values acquired from gauge heads one by one according to the measurement without mechanically limiting the cylinder centers as the measurement reference position. Hence, since there is no need of limiting the above mentioned cylinder center, that is, the measurement reference position exactly according to the measuring method of the present invention, it is possible to measure a circumferential shape of a cylinder with high accuracy simply without accompanying such any loads.

In addition, in the method which the present invention provides, since each measured value can obtain measurement result which is directly measured without being approximately calculated, each measured value is not influenced by the number of measurement points. Because of this, the number of measurement points at the time of measuring a circumferential shape (dimensional accuracy) of the above-mentioned cylinder which is premised on having high accuracy originally like an object of the present invention can be performed measurement required for accuracy assurance of a product at the necessary minimum number of measurement points. Hence, in performing the accuracy measurement of a cylinder as industrial product evaluation, it can be said that the present invention is very ideal from a viewpoint of pursuing measurement efficiency.

Furthermore, according to the second embodiment of the present invention, there is provided a measuring method of a shape of a cross-sectional circle, which is orthogonal to an axis of a cylinder to be measured, by the following steps (i) to (v) using measuring means constructed of (a) a cylinder support jig, and (b) a mount having first, second, third and fourth sensors for detecting displacements, which are located on a cross section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the third sensor and the fourth sensor are θ°, comprising: (i) a step of measuring each of distances $\Delta L1$, $\Delta L2$, $\Delta L3$ and $\Delta L4$ between each of the first, second, third and fourth sensors and intersecting points of lines connecting the respective sensors and the $O_0$ with a circumference of the cross-sectional circle of the cylinder to be measured, (ii) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$L1 = LS1 - \Delta L1$, $L2 = LS2 - \Delta L2$, $$L3=LS3-\Delta L3,$$

$$L4=LS4-\Delta L4,$$

wherein LS1, LS2, LS3 and LS4 are distances between each of the first, second, third and fourth sensors and the $O_0$, (iii) a step of rotating the cylinder to be measured by θ° in a direction toward the second sensor from the first sensor, and repeating the steps (i) and (ii), (iv) a step of calculating a distance ΔO1 between a floating point O', which is a point on the cross-sectional circle of the cylinder to be measured corresponding to the $O_0$ before the rotation in the step (iii), and a line passing through the $O_0$ and intersecting at right-angle with the line connecting the first sensor and the $O_0$, from L1 and L3 obtained in the step (ii) and L2 and L4 obtained in the step (iii), (v) a step of calculating a distance between the O' and a line intersecting at right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and ΔO1 obtained in the step (iv).

In addition, as a third aspect of the present invention, the present inventors found out that, in addition to not limiting the above-mentioned measurement reference position, high accuracy was not required about positioning of gauge heads to the measured cylinder, and it was possible to perform measurement, which was equivalent to that both of positional relation of gauge heads to the measured cylinder and positional relation between gauge heads were accurate, by using a cylindrical body different from the measured cylinder a shape of whose cross-sectional circle which is orthogonal to the above-mentioned axis is a true circle.

Specifically, it is a method for determining a shape of a cross-sectional circle, which is orthogonal to an axis of a cylinder to be measured, by the following steps (i) to (vii) using measuring means constructed of (a) a cylinder support jig, and (b) a mount having first, second and third sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the second sensor and the third sensor are θ°, the cross-sectional circle of the reference cylinder being a true circle having a radius of d2, comprising: (i) a step of measuring each of distances ΔLR1, ΔLR2 and ΔLR3 between each of the first, second and third sensors and intersecting points of lines connecting the respective sensors and the $O_0$ with a circumference of the cross-sectional circle of the reference cylinder, (ii) a step of calculating each of distances LS1, LS2 and LS3 between each of the first, second and third sensors and the $O_0$ according to the following equations:

$$LS1=d2+\Delta LR1,$$

$$LS2=d2+\Delta LR2,$$

$$LS3=d2+\Delta LR3,$$

(iii) a step of measuring each of distances ΔL1, ΔL2 and ΔL3 between each of the first, second and third sensors and intersecting points of lines connecting the respective sensors and the $O_0$ with a circumference of the cross-sectional circle of the cylinder to be measured, (iv) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$$L1=LS1-\Delta L1,$$

$$L2=LS2-\Delta L2,$$

$$L3=LS3-\Delta L3,$$

(v) a step of rotating the cylinder to be measured by θ° in a direction toward the second sensor from the first sensor, and repeating the steps (iii) and (iv), (vi) a step of calculating a distance ΔO1 between a floating point O', which is a point on the cross-sectional circle of the cylinder to be measured corresponding to the $O_0$ before the rotation in the step (v), and a line passing through the $O_0$ and intersecting at right-angle with the line connecting the first sensor and the $O_0$, from L1 and L2 obtained in the step (iv) and L2 and L3 obtained in the step (v), (vii) a step of calculating a distance between the O' and a line intersecting at right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and ΔO1 obtained in the step (vi).

In addition, according to the fourth embodiment of the present invention, there is provided a method for determining a shape of a cross-sectional circle, which is orthogonal to an axis of a cylinder to be measured, by the following steps (i) to (vii) using measuring means constructed of (a) a cylinder support jig, and (b) a mount having first, second, third and fourth sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the third sensor and the fourth sensor are θ°, the cross-sectional circle of the reference cylinder being a true circle having a radius of d2, comprising: (i) a step of measuring each of distances ΔLR1, ΔLR2, ΔLR3 and ΔLR4 between each of the first, second, third and fourth sensors and intersecting points of lines connecting the respective sensors and the $O_0$ with a circumference of the cross-sectional circle of the reference cylinder, a step of calculating each of distances LS1, LS2, LS3 and LS4 between each of the first, second, third and fourth sensors and the $O_0$ according to the following equations:

$$LS1=d2+\Delta LR1,$$

$$LS2=d2+\Delta LR2,$$

$$LS3=d2+\Delta LR3,$$

$$LS4=d2+\Delta LR4,$$

(iii) a step of measuring each of distances ΔL1, ΔL2, ΔL3 and ΔL4 between each of the first, second, third and fourth sensors and intersecting points of lines connecting the respective sensors and the $O_0$ with a circumference of the cross-sectional circle of the cylinder to be measured, (iv) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$$L1=LS1-\Delta L1,$$

$$L2=LS2-\Delta L2,$$

$$L3=LS3-\Delta L3,$$

$$L4=LS4-\Delta L4,$$

(v) a step of rotating the cylinder to be measured by $\theta°$ in a direction toward the second sensor from the first sensor, and repeating the steps (iii) and (iv), (vi) a step of calculating a distance $\Delta O1$ between a floating point O', which is a point on the cross-sectional circle of the cylinder to be measured corresponding to the $O_0$ before the rotation in the step (v), and a line passing through the $O_0$ and intersecting at right-angle with the line connecting the first sensor and the $O_0$, from L1 and L3 obtained in the step (iv) and L2 and L4 obtained in the step (v), (vii) a step of calculating a distance between the O' and a line intersecting at right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and $\Delta O1$ obtained in the step (vi).

Furthermore, according to the fifth embodiment of the present invention, there is provided a measuring method of a shape of a cross-sectional circle, which is orthogonal to an axis of a cylinder to be measured, according to the first embodiment, further comprising the following step (vi): (vi) a step of repeating once or two or more times the steps (i) to (v), and obtaining the distance between the O' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (iii).

According to the sixth embodiment, there is provided a measuring method of a shape of a cross-sectional circle, which is orthogonal to an axis of a cylinder to be measured, according to the second embodiment, further comprising the following step (vi): (vi) a step of repeating once or two or more times the steps (i) to (v), and obtaining the distance between the O' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (iii).

According to the seventh embodiment of the present invention, there is provided a measuring method of a shape of a cross-sectional circle, which is orthogonal to an axis of a cylinder to be measured, according to the third embodiment, further comprising the following step (viii): (viii) a step of repeating once or two or more times the steps (iii) to (vii), and obtaining the distance between the O' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (v).

According to the eighth embodiment of the present invention, there is provided a measuring method of a shape of a cross-sectional circle, which is orthogonal to an axis of a cylinder to be measured, according to the fourth embodiment, further comprising the following step (viii): (viii) a step of repeating once or two or more times the steps (iii) to (vii), and obtaining the distance between the O' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (v).

According to the ninth embodiment of the present invention, there is provided a measuring method of a cylindrical shape of a cylinder to be measured by measuring shapes of a plurality of cross-sectional circles, which are orthogonal to an axis of a cylinder to be measured, characterized in that the measuring method of shapes of a plurality of cross-sectional circles is carried out according to any one of the first to eighth embodiments.

The above-described "to calculate a circumferential shape of a cross-sectional circle" means, for example, to obtain a circle center position of a cross-sectional circle by a method of least squares, or to obtain a roundness.

In addition, suppose that all the distances described with a sensor, such as a distance measured by a sensor, and a distance which indicates a position of a sensor, among distances described in this specification are described on the basis of a reference position on a measurement function of each sensor. An example of the distances is a distance to an object from a portion, which does not operate by a displacement of a measuring object, among members which construct a sensor and are shown by an arrow in each drawing such as FIG. 26 showing such a stylus type sensor that is represented by an electric micrometer, or FIG. 27 showing such a non-contact sensor that is represented by an eddy current type sensor.

Most of conventional measuring methods require loads so as to pursue accuracy of mechanical limitation of a cylinder center as a measurement reference position for the purpose of acquiring the higher accuracy of measurement. On the other hand, methods which the present invention provides premise that this cylinder center is a virtual center, i.e., a center which may move by rotation. That is, as shown in FIG. 1, when a cylinder is rotated by a predetermined angle ($\theta°$) with a starting point of a floating point as a reference point, the floating point moves from the starting point. When it is rotated further again, the floating point moves further. When it is rotated sequentially for the cylinder to be rotated finally at 360°, the floating point takes a track of the floating point which is shown in the figure. Therefore, the measuring method of the present invention can specify a shape of a circle, which is a measuring object, by tracking, and theoretically catching a position of this floating point, and calculating distances between the floating point and points on the circumference of the circle each time the measured cylinder rotates by one notch on the basis of the change of numerical values acquired from gauge heads one by one according to the measurement without mechanically limiting the measurement reference position. Hence, according to the methods of the present invention, since there is no need of limiting exactly the above-mentioned cylinder center, that is, a measurement reference position, it is possible to measure a cylinder with high accuracy simply without accompanying such any loads. In addition, in the methods which the present invention provides, a rotation method in the measurement of a measured cylinder is not limited. Hence, it is possible to perform measurement in a state of making both end sections free, or in a state of mounting parts such as a flange. Hence, even if a measuring mechanism using a measuring method of the present invention is mounted in a production line, it is possible to perform highly precise measurement very simply without problems such as an interference with conveyance means.

In addition, the "rotation axis", "cylinder axis", and "point" where they intersects, which are used in this specification do not point out, for example, a straight line without thickness and a point without an area which are used mathematically. For example, as shown in FIG. 2, when a measured cylinder 1 rotates on the basis of its own outer periphery, unless the measured cylinder is at least a perfect cylinder or an outer periphery abutting on runners 6 is a perfect circular shape, the rotation axis and the point have certain ranges.

Hereafter, numerical values which show the ranges will be explained. When a circle whose radius is made $\Delta L$ is shown as a range with a least-square circle center of a measured cross-sectional circle as a center, the range of the rotation axis preferably fulfills the following formula and $\Delta L' < d \cdot 10^{-3}$. Further, more preferably, it fulfills the following formula and $\Delta L' < d \cdot °\Delta 10^{-4}$, or most preferably, fulfills the following formula and $\Delta L' < d \cdot °\Delta 10^{-5}$.

$$d - \Delta L' = \sqrt{d^2 - (\Delta L - T)^2}$$

d: Mean radius value of cross-sectional circle measured,
T: Cylindricity of measured cylinder For example, assuming that d=50.00 mm and T=0.05 mm, a range of the rotation axis in a most preferable case is $\Delta L' < 0.0005$ mm and $\Delta L < 0.274$ mm, and a range of the rotation axis by calculation is 0.548 mm.

In addition, as reality of $\Delta L$, positioning of a sensor in such accuracy is a possible range without any problem in view of a level of present machining technology (a general limit in this industry is about $\Delta L \approx 0.002$ mm in the case of d=50 mm).

In addition, with regard to the cross-sectional circle with the true circle shape which the above-mentioned cylinder 2 has, although it is most preferable that its circularity is 0, it is impossible to form such a cross-section industrially. About this, when describing a range of a circularity with being premised on the resolution in measurement results by the measuring method of the present invention, preferably, it is $2 \times 10^{-3}$% to an average diameter of a circle, and more preferably, it is $1 \times 10^{-3}$%.

BRIEF DESCRIPTION OF THE DRAWINGS

FIG. 10 shows data from measured values of sensors for detecting displacements to coordinate positions of circle centers in samples 1 to 5 which are obtained in example 1.

FIG. 11 shows data from measured values of sensors for detecting displacements to coordinate positions of circle centers in samples 6 to 10 which are obtained in example 1.

FIG. 12 shows rectangular coordinate positions of respective points on the basis of center coordinate positions, distances to respective points, and their maximum values and minimum values in samples 1 to 5 obtained in example 1.

FIG. 13 shows rectangular coordinate positions of respective points on the basis of center coordinate positions, distances to respective points, and their maximum values and minimum values in samples 6 to 10 obtained in the first embodiment.

FIG. 16 shows measurement durations and difference which were obtained in example 1 and first comparative example.

FIG. 18 shows distances from sensors for detecting displacements to the surface of the measured cylinder which were obtained in example 2.

FIG. 19 shows differential values which were generated by the rotation in FIG. 17 and were obtained in example 2, and numerical values which were obtained by subtracting the differential values from a constant to be made positive integers.

FIG. 20 shows displacement amounts of the surface of a measured cylinder 1 on the basis of a floating point which were obtained in example 2.

FIG. 21 shows the coordinate value and distances which were obtained in example 2 and were obtained by converting FIG. 20 into the rectangular coordinate position.

FIG. 23 shows the measured distance from each measurement point to the measurement reference position $O_0$ in the third example.

FIG. 24 shows data from measured values of each of the above-mentioned sensors to the above-mentioned circle center coordinate positions among data obtained by the measurement in the third example.

FIG. 25 shows distances of the X axial component and Y axial component from the above-mentioned center coordinate position to each point, distances to each point, maximum and minimum values of them, circularities, and outer diameter values, which were obtained in the measurement in the third example.

FIG. 28 shows distances of the above-mentioned respective intersections and respective measuring points on a circumference at each coordinate position, a maximum value, and a minimum value, which were obtained in example 5.

DESCRIPTION OF THE PREFERRED EMBODIMENTS

The following description is one embodiment of a method used in the present invention, and those skilled in the art should be able to easily understand that the same effect will be obtained also in other forms.

Figure 1:
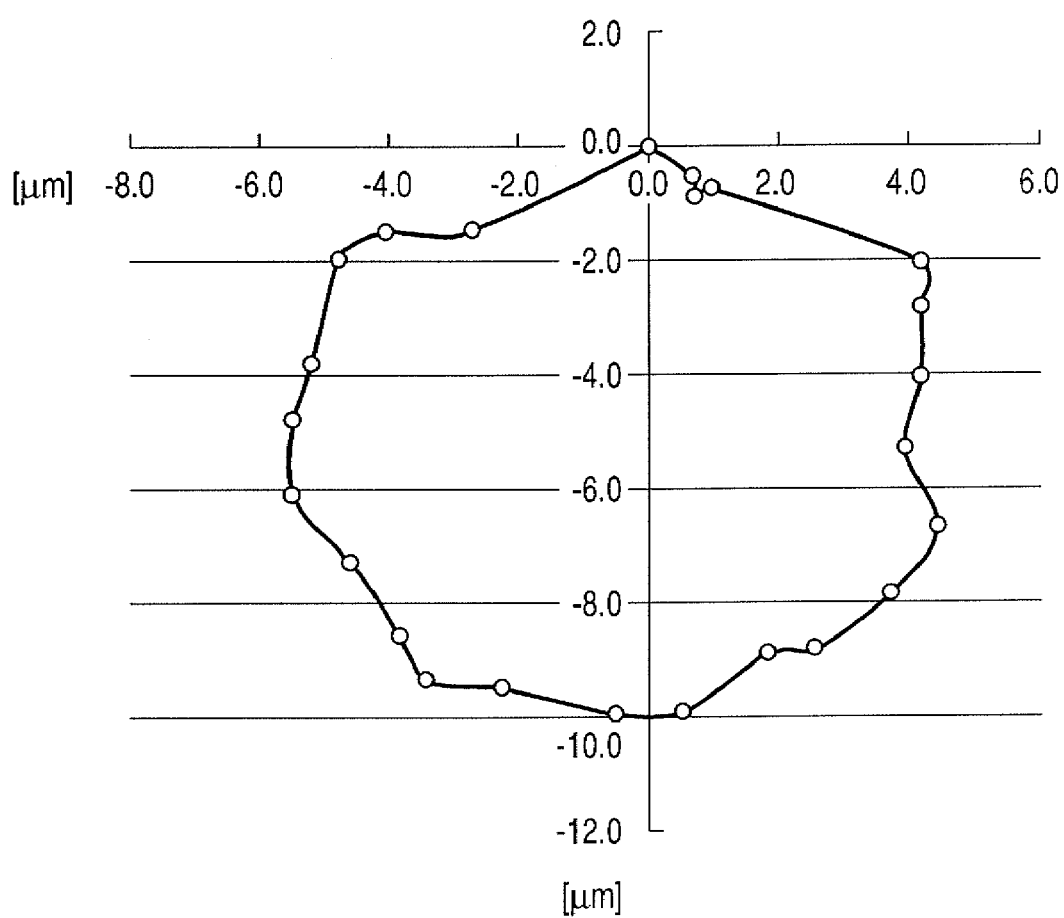
FIG. 1 is a graph showing a locus of movement of an actual floating point on the basis of a starting point of the floating point by 360° rotation of a cylinder at the time of the measured cylinder being rotated by a predetermined angle.
Figure 2:
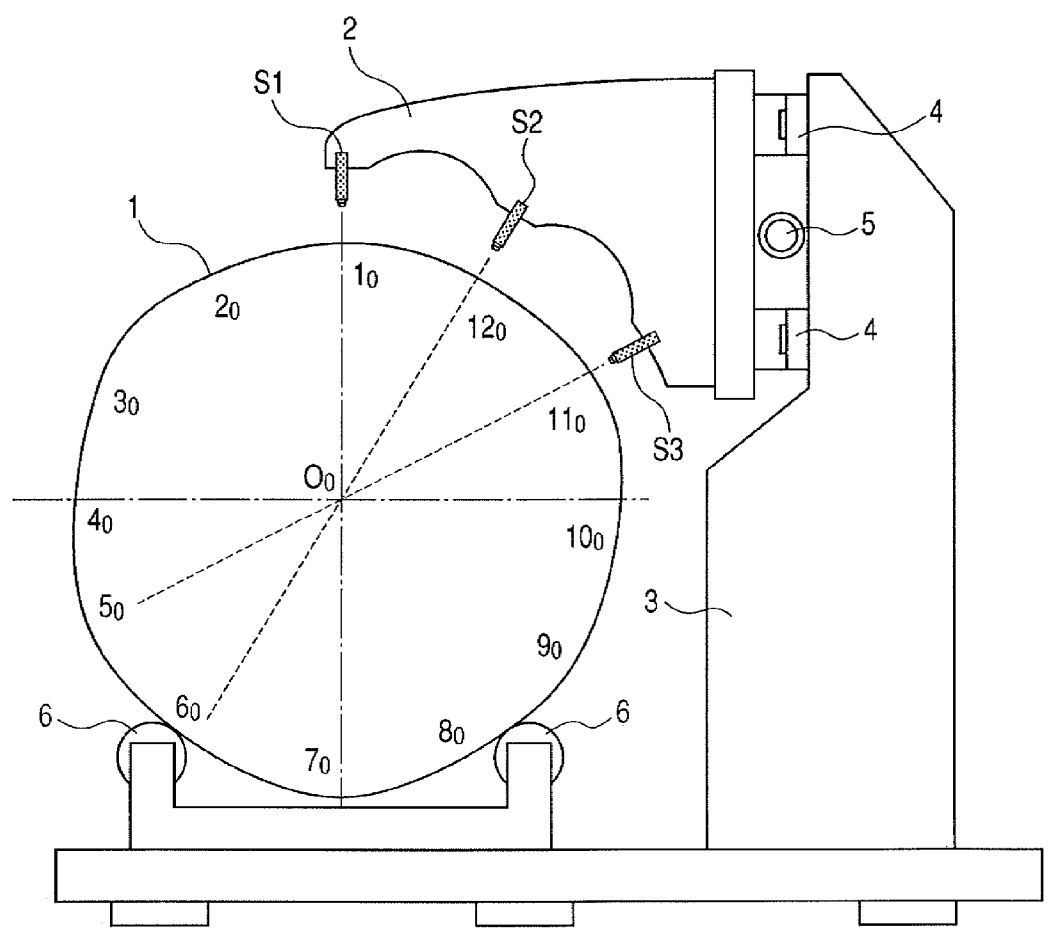
FIG. 2 is a schematic diagram of a measuring apparatus.

FIG. 2 shows an example of an apparatus used for the shape measurement of a cross-sectional circle of a cylinder which relates to this embodiment. The measuring apparatus concerned receives a measured cylinder 1 on rotatable cylinder support jigs (runners 6), and has three sensors S1, S2 and S3 for detecting displacements which are located on the same cross-section, which is orthogonal to a rotation axis of the measured cylinder 1, on a mount 2 mounted reciprocably in parallel to the rotation axis of the measured cylinder 1 by guide rails 4 and a ball screw 5, which are oriented to a measurement reference point $O_0$ which is an intersection of the rotation axis of the measured cylinder 1, and the cross-section orthogonal to the rotation axis, and which are arranged in a shape formed by connecting a measurement reference point ($O_0$) and three sensors being a fan shape with forming a predetermined angle ($\theta°$) with the measurement reference point $O_0$ as a center and are fixed to the mount 2. The three sensors S1, S2 and S3 for detecting displacements, and rotation centers of two runners 6 are being fixed to the same machine, and their mutual positions always do not change.

In addition, the measurement reference point $O_0$ is a point, on which the detection axes of the above-mentioned three sensors almost intersect mutually, and a measurement reference position which never moves with conforming to a machine datum. At the same time, it is a starting point (hereafter, this is described as $O_{n=0}$) of a virtual center which moves as the measured cylinder 1 which is not a true circle rotates on runners 6 in connection with measurement, that is, a floating point $O_n$. Unless the measured circle in the measured cylinder 1 is in a true circle shape, the position of a floating point $O_n$ sequentially moves as the measured cylinder 1 rotates in connection with measurement, but a distance between $O_n$ and each point on a circumference never changes.

Figure 3:
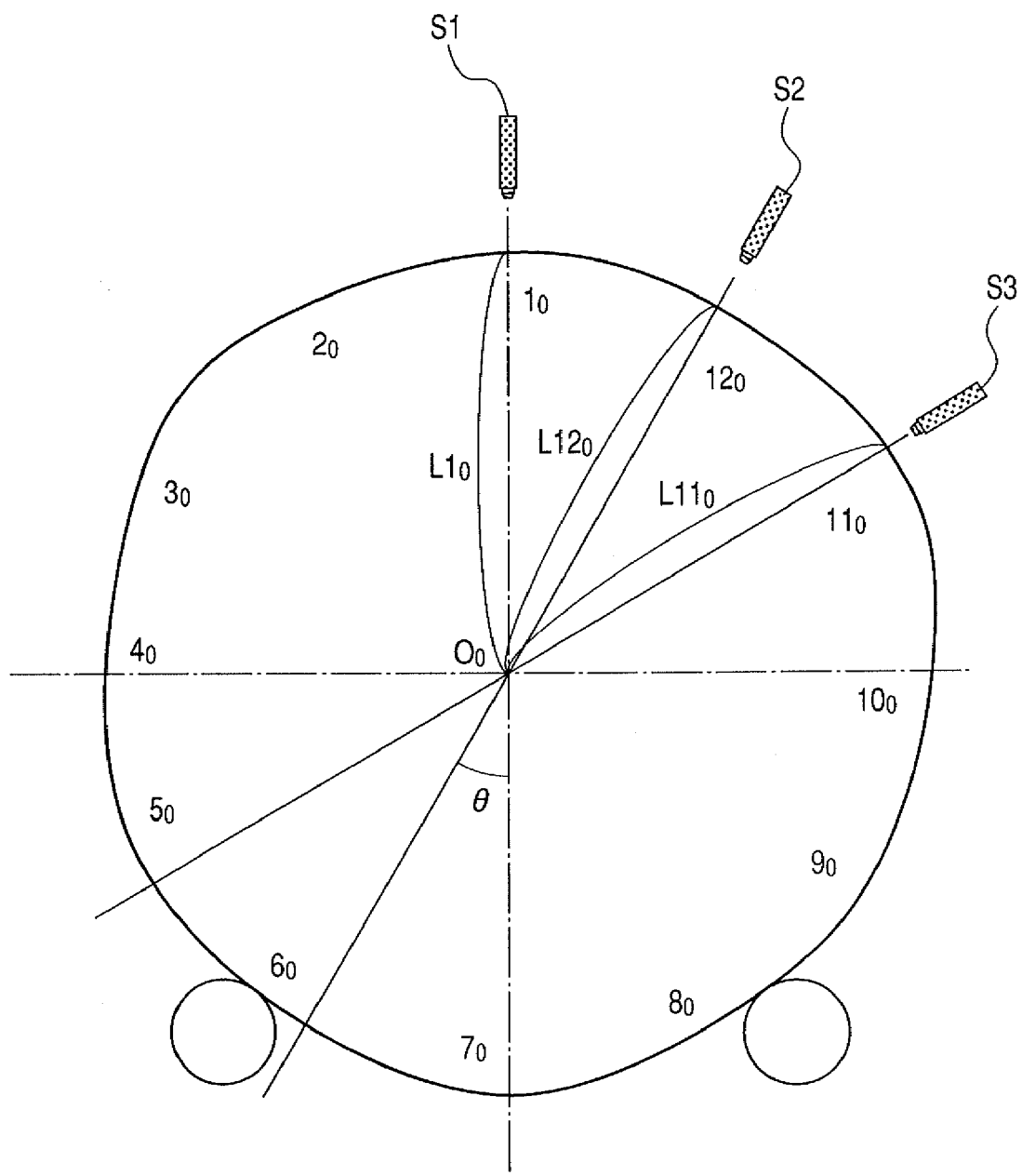
FIG. 3 is an explanatory diagram of measuring points.

Next, a measuring method of a shape of a cross-sectional circle of the cylinder concerned which is orthogonal to an axis will be described. Here, a rotation angle $\theta°$ per one measurement of the measured cylinder 1 was set at 30°. Hence, measuring points on a circumference become 12 points $1_0$ to $12_0$ as shown in FIG. 3. Then, this measuring method calculates distance from a starting point ($O_{n=0}$) of a floating point to points $2_0$ on the circumference of a measured circle to finally calculate distance from a starting point ($O_{n=0}$) of a floating point to respective points $1_0$ to $12_0$.

As a first stage, distances $L1_0$, $L12_0$ and $L11_0$ between $O_0$ ($O_{n=0}$) and the points $1_0$, $12_0$, and $11_0$ on a circumference of the measured circle are measured by using the sensors S1, S2 and S3 for detecting displacements.

Figure 4:
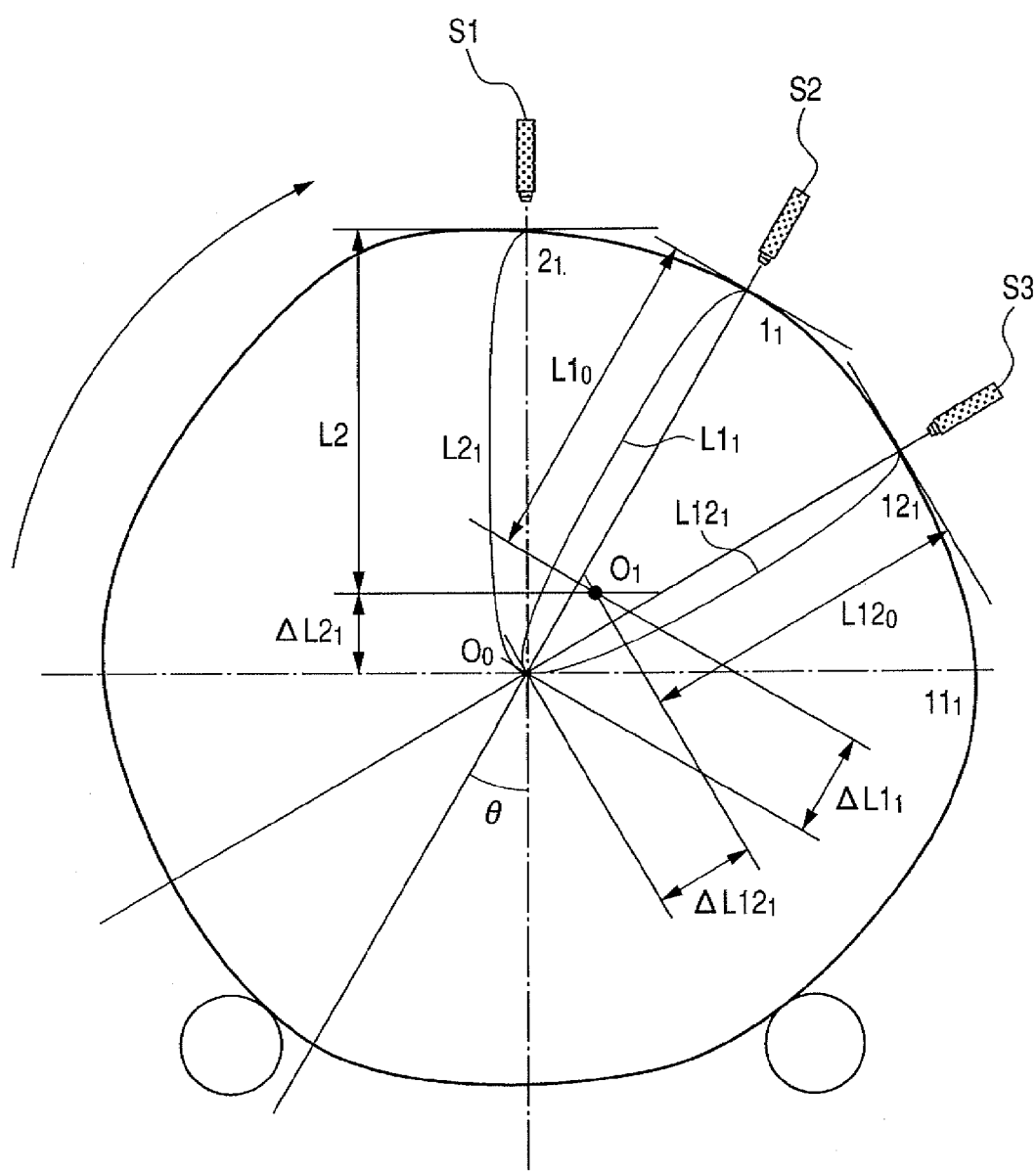
FIG. 4 is an explanatory diagram relating to the movement of a floating point.

As a second stage, when the cylinder is rotated rightward by 30°, the measuring points $1_0$, $12_0$, and $11_0$ on the circumference in the first stage move to $1_1$, $12_1$, and $11_1$ respectively, and the sensors S1, S2 and S3 for detecting displacements become ready to measure distances between points $2_1$, $1_1$ and $12_1$ on the circumference and the measurement reference point $O_0$ respectively, as shown in FIG. 4. At this time, assuming that the floating point $O_{n=0}$ does not coincide with a true center of the measured circle, or that the measured circle is not truly round, $O_n$ moves to $O_{n=1}$. At this time, the distance between the floating point $O_{n=o}$ and the point $2_1$ on the circumference is unknown. Next, the distances $L2_1$, $L1_1$ and $L12_1$ between the points $2_1$, $1_1$ and $12_1$ on the circumference and the measurement reference point $O_0$ are respectively measured using the sensors S1, S2 and S3 for detecting displacements.

Here, a position of a current position $O_{n=1}$ of the floating point $O_n$ is obtained from the change of respective distances by rotation. Since $L1_0$ and $L12_0$ are known, it is possible to obtain moving distances $\Delta L1_1$ and $\Delta L12_1$ from $O_{n=o}$ to $O_{n=1}$ on each detection axis of the sensors S2 and S3 for detecting displacements.

$$\Delta L1_1 = L1_1 - L1_0 \tag{1}$$

$$\Delta L12_1 = L12_1 - L12_0 \tag{2}$$

Figure 5:
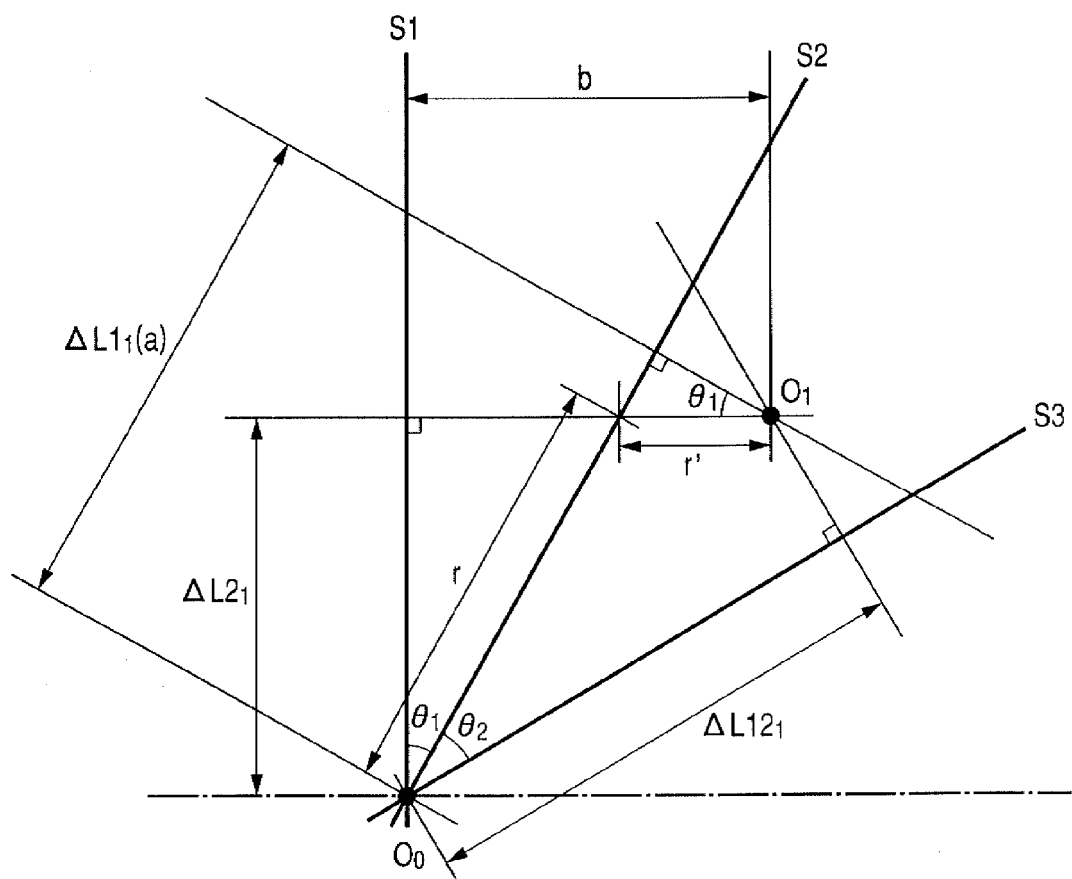
FIG. 5 is an explanatory diagram (1) relating to the calculation of a floating centre position.

Hereinafter, a moving distance $\Delta L2_1$ of the floating point $O_{n=1}$ on the detection axis of the sensor S1 for detecting a displacement is obtained using these two distances. Then, a distance between the floating point $O_{n=0}$ and the point $2_0$ on the circumference can be obtained by taking the difference between $L2_1$ and $\Delta L2_1$. Thus, as shown in FIG. 5, let $\Delta L1_1$ be a, and let the shortest distance between the detection axis of the sensor S1 for detecting a displacement and the floating point $O_{n=1}$, that is, a moving distance in an x-axial component of the floating point $O_{n=1}$ expressed in rectangular coordinates where the detection axis of the sensor S1 for detecting a displacement is made a y-axis be b. When expressing a and b using r and r' shown in FIG. 5, respectively:

$$r' \cdot \sin \theta_1 + r = a \tag{3}$$

$$r' + r \cdot \sin \theta_1 = b \tag{4}$$

$$r' = (b - a \cdot \sin \theta_1)/(\cos^2 \theta_1) \tag{5}$$

$$r = a - \sin \theta_1 \cdot [(b - a \cdot \sin \theta_1)/(\cos^2 \theta_1)] \tag{6}$$

Furthermore, from FIG. 5, since being $\Delta L2_1 = r \cdot \cos \theta_1$, $$\Delta L2_1 = a \cdot \cos \theta_1 - \tan \theta_1 (b - a \cdot \sin \theta_1) \tag{7}$$

Figure 6:
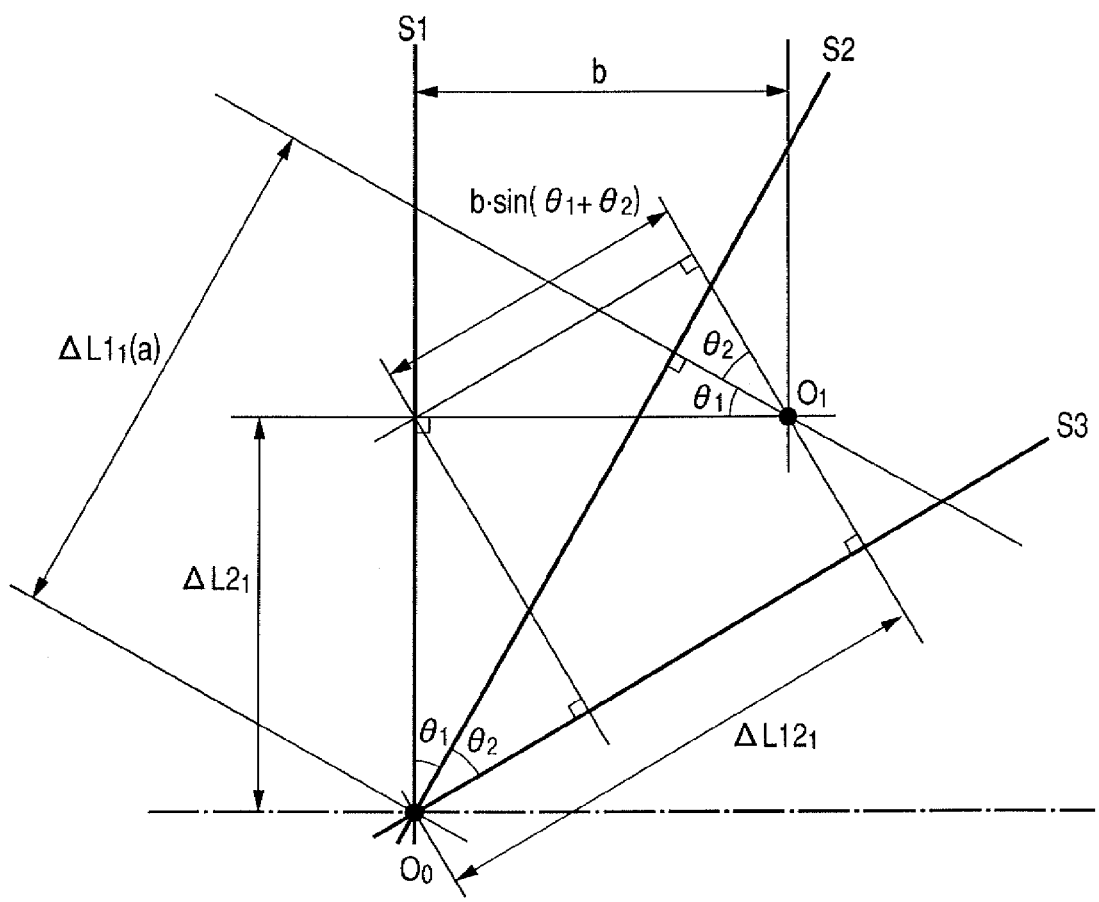
FIG. 6 is an explanatory diagram (2) relating to the calculation of a floating centre position.

Here, from FIG. 6, $$\Delta L12_1 - b \cdot \sin(\theta_1 + \theta_2) = \Delta L2_1 \cdot \cos(\theta_1 + \theta_2) \tag{8}$$

$$\Delta L2_1 = [\Delta L12_1 - b \cdot \sin(\theta_1 + \theta_2)]/[\cos(\theta_1 + \theta_2)] \tag{9}$$

$$a \cdot \cos \theta_1 - \tan \theta_1 \cdot (b - a \cdot \sin \theta_1) = [\Delta L12_1 - b \cdot \sin(\theta_1 + \theta_2)]/[\cos(\theta_1 + \theta_2)] \tag{10}$$

$$b = [a \cdot (\cos \theta_1 + \sin \theta_1 \cdot \tan \theta_1) \cdot \cos(\theta_1 + \theta_2) - \Delta L12_1]/[\tan \theta_1 \cdot \cos(\theta_1 + \theta_2) - \sin(\theta_1 + \theta_2)] \tag{11}$$

Hence, $\Delta L2_1$ can be obtained with arguments included in the following two formulas, that is, a mutually forming angle and measured values of the sensors for detecting displacement.

From the above-mentioned formula 7, $$\Delta L2_1 = \Delta L1_1 \cdot \cos \theta_1 - \tan \theta_1 \cdot (b - \Delta L1_1 \cdot \sin \theta_1) \tag{12}$$

$$b = [\Delta L1_1 \cdot (\cos \theta_1 + \sin \theta_1 \cdot \tan \theta_1) \cdot \cos(\theta_1 + \theta_2) - \Delta L12_1]/[\tan \theta_1 \cdot \cos(\theta_1 + \theta_2) - \sin(\theta_1 + \theta_2)] \tag{13}$$

From $\Delta L2_1$ obtained using the above-mentioned formulas 12 and 13, $L2_0$ is obtained as $L2_0 = L2_1 - \Delta L2_1$.

As a third step, the measured cylinder is rotated further by 30° rightward. Then, the measuring points $2_1$, $1_1$ and $12_1$ on the circumference in the above-mentioned second stage are respectively moved to $2_2$, $1_2$ and $12_2$, and the sensors S1, S2, and S3 for detecting displacements become ready to measure distances between the points $3_2$, $2_2$ and $1_2$ on the circumference and the measurement reference point $O_0$ respectively. In addition, the floating point $O_{n=1}$ further moves to $O_{n=2}$. Next, distances between the points $3_2$, $2_2$ and $1_2$ on the circumference and the measurement reference point $O_0$ are respectively measured using the sensors S1 to S3 for detecting displacements. A moving distance from the floating point $O_{n=0}$ to $O_{n=2}$ is calculated by the same method as the above-described method using these measured values. Furthermore, by using the calculation result, a moving distance ($\Delta L3_2$) of $O_{n=2}$ from $O_{n=0}$ on the measurement axis (y-axis) of the sensor S1 for detecting a displacement is obtained, and a distance between the floating point $O_{n=0}$ and the point $3_0$ on the circumference is obtained from there. Hereinafter, similarly, the cylinder is rotated by 30° at a time for distances $L4_0$, $L5_0$, $L6_0$, $L7_0$, $L8_0$, $L9_0$ and $L10_0$ between the floating point $O_{n=0}$ and points $4_0$, $5_0$, $6_0$, $7_0$, $8_0$, $9_0$ and $10_0$ on the circumference to be obtained, respectively. When calculating $L11_0$ and $L12_0$ using the same method at this time, the measurement result with higher accuracy can be obtained.

In addition, according to another method provided by the present invention, it is possible to perform measurement, which is equivalent to that both of the positional relation of gauge heads to the measured cylinder and positional relation between gauge heads were accurate, by using a cylindrical body different from the measured cylinder a shape of whose cross-sectional circle which is orthogonal to the above-mentioned shaft is a true circle.

Figure 7:
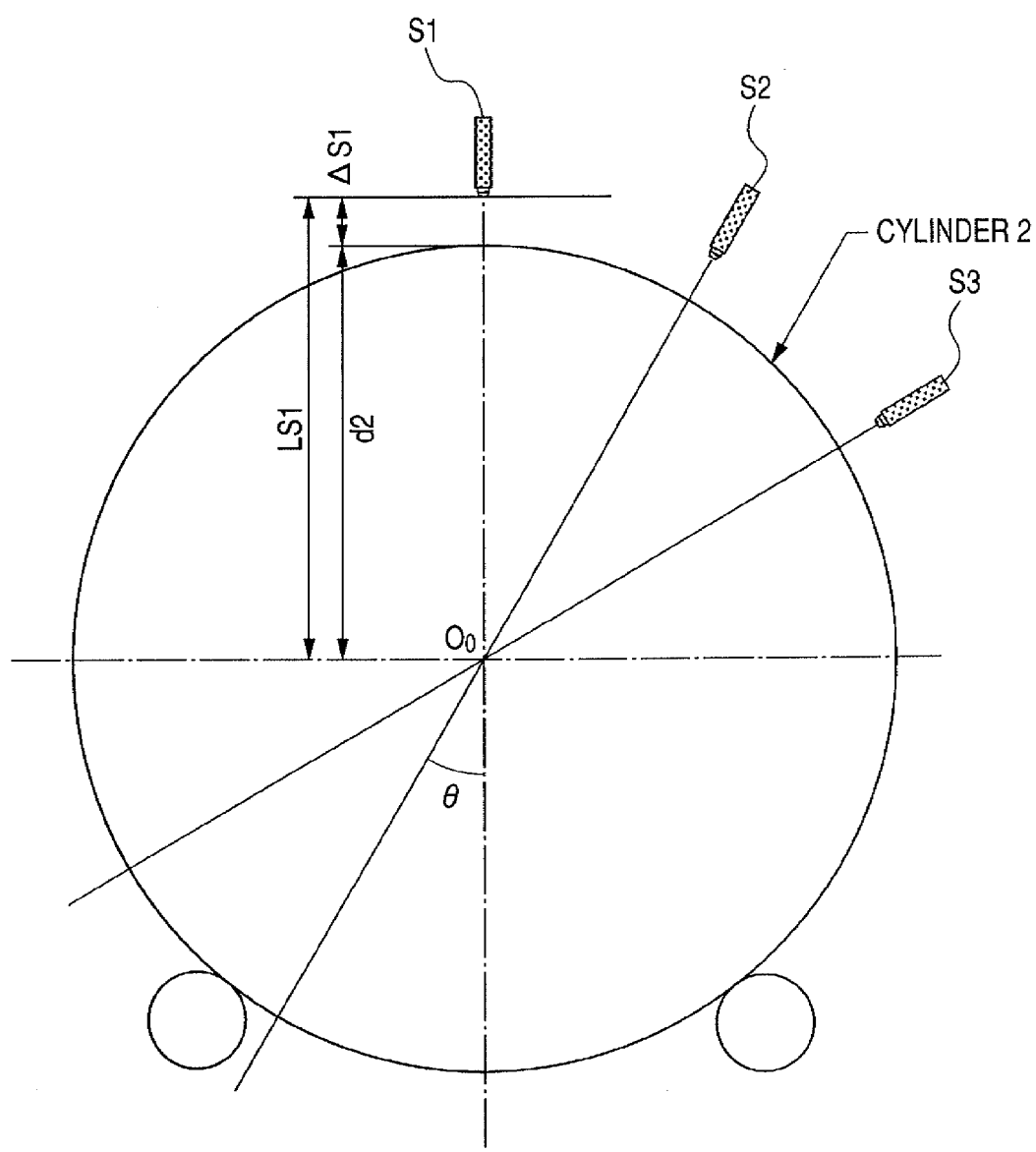
FIG. 7 is a diagram showing positions of a second cylinder and sensors.

First, as shown in FIG. 7, with letting a cross-sectional circle center of the cylinder 2 be the above-mentioned measurement reference point $O_{n=0}$ using a cylinder 2 as a reference cylinder whose sectional shape is a true circle shape, distances from sensors S1, S2, and S3 to $O_{n=0}$ are limited. On this occasion, first, with placing the cylinder 2 on the above-mentioned two runners 6, a distance from the sensor S1 to an outer surface of the above-mentioned cylinder 2 is measured to make it $\Delta S1$. Since an outer diameter value of the cylinders 2 is known, let its radius value, that is, a distance from the circle center $O_{n=0}$ to the outer surface of the cylinder 2 be d2, and a distance LS1 from the sensor S1 to $O_{n=0}$ is obtained as the following formula A:

$$LS1 = \Delta S1 + d2$$

Similarly, LS2 and LS3 are obtained also about sensors S2 and S3.

Figure 8:
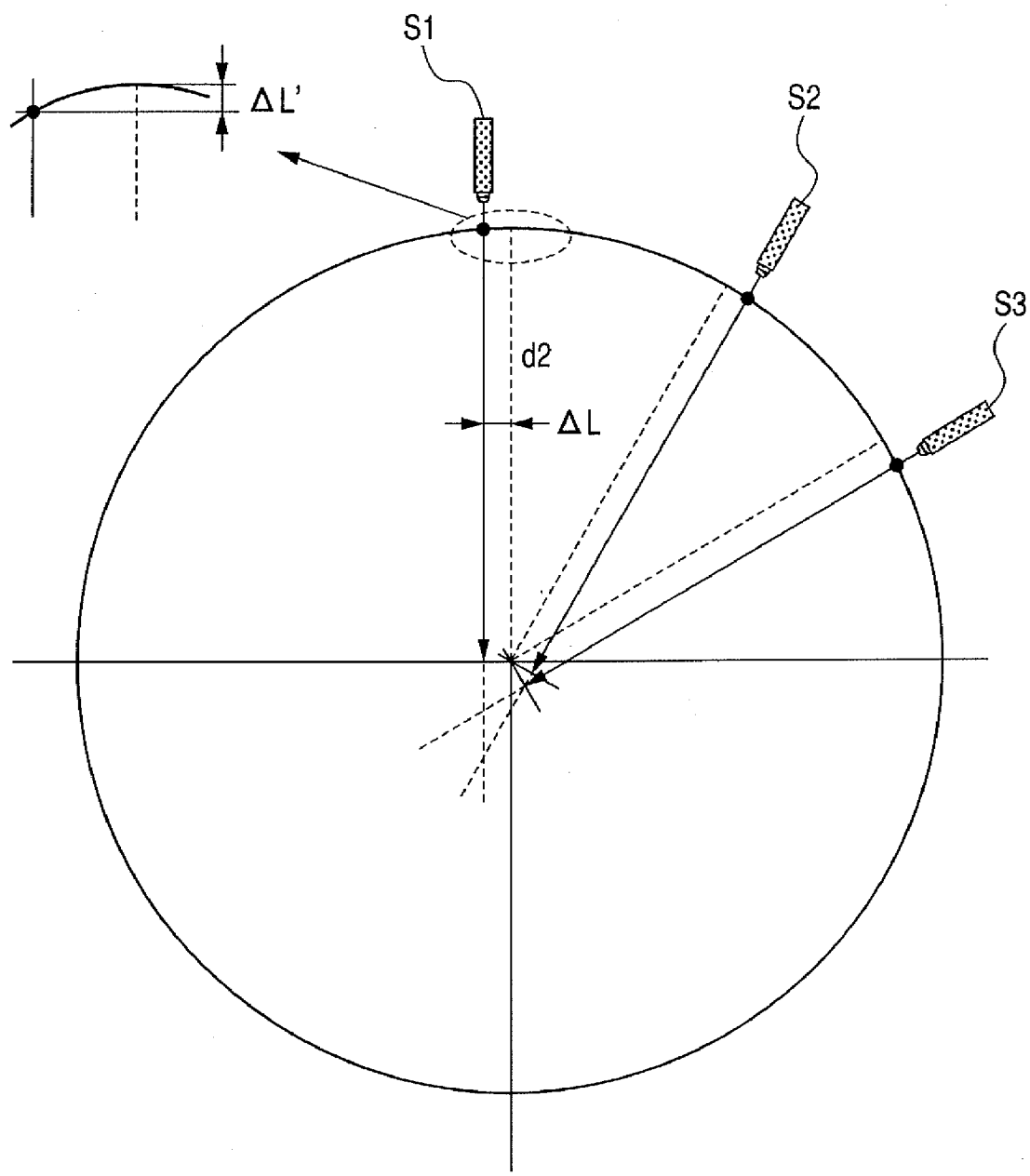
FIG. 8 is a diagram showing positioning errors of the sensors.

At this time, when three detection axes do not intersect at one point mutually without any detection axis of the sensors S1, S2, and S3 passing the above-mentioned measurement reference position $O_{n=0}$, this positional displacement of the measurement reference position $O_{n=0}$ to the detection axes generates errors in values of the above-mentioned LS1, LS2, and LS3. Nevertheless, the errors are extremely small and will be described using FIG. 8 by making LS1 an example about this. Let a minimum distance between the measurement reference position $O_{n=0}$, which is the circle center of the cross-sectional circle of the cylinder 2, and the detection axis of the sensor S1, that is, a positioning error distance of the sensor S1 in a direction, orthogonal to the detection axis, be $\Delta L$, and let a distance between a point on which an axis which is parallel to the detection axis and passes the measurement reference position $O_{n=0}$ intersects a circumference, and the measurement reference position $O_{0=0}$, that is, a radius distance of the cross-section of the cylinder 2 be d2, and an error $\Delta L'$ given to LS1 is given as the following formula B:

$$\Delta L' = d2 - \sqrt{(d2^2 - \Delta L^2)}$$

and $\Delta L'$ is extremely small.

In addition, an error arising by positioning processing of the gauge head should be mentioned also about an angle error besides the above-mentioned positioning error. With separating this from the above-mentioned positioning error, the above-mentioned $\Delta L$ which derives from only the angle error to the detection axis of the sensor S1 is given as the following formula C:

$$\Delta L = \Delta S1 \cdot \tan \theta$$

For example, generally an angle error supposed in the case of positioning a sensor using a stylus type sensor with a resolution of about 1 μm, or the like is ±14 seconds ($3.9 \times 10^{-3}$°) approximately, and $\Delta L$ becomes 0.068 μm when the distance $\Delta S1$ between the sensor S1 and the outer surface of the cylinder 2 is about 1.0 mm. At this time, when an outer diameter of the cylinder 2 is 100 mm, $\Delta L'$ is about $4.6 \times 10^{-3}$ μm from the above-mentioned formula C, which can be said that this is extremely small as an error. In addition, also in the case that this $\Delta L$ is caused by a circularity of the cross-section of the cylinder 2, an influence which is given to a measurement result is similar.

Hence, even if the own detection axis has not passed through the circle center of the cross-sectional circle of the cylinder 2 in the measuring systems in a range described until now, the sensor S1 can perform measurement with making the circle center the measurement reference position $O_{n=0}$. In addition, from the above, it is possible to handle similarly the LS2 and LS3. Furthermore, a moving distance of the above-mentioned floating point $O_n$ is calculated with numerical values of the above-mentioned LS1, LS2, and LS3 to the last, but are never influenced by the distance of the above-mentioned $\Delta L$.

Subsequently, with placing the measured cylinder 1 on the above-mentioned two runners 6, a distance from the sensor S1 to an outer surface of the above-mentioned cylinder 1 is measured to be made $S1_0$. Since LS1 is known at this time, the above-described $L1_0$ is calculated by subtracting $S1_0$ from LS1, and similarly, $L12_0$ and $L11_0$ are measured and calculated.

After that, by advancing measurement similarly to the method after the above-mentioned second stage, it is possible to obtain distances $L4_0$, $L5_0$, $L6_0$, $L7_0$, $L8_0$, $L9_0$, and $L10_0$ between the floating point $O_{n=0}$ and points on the circumference $4_0$, $5_0$, $6_0$, $7_0$, $8_0$, $9_0$, and $10_0$, respectively.

Here, when the above-mentioned cylinder 2 has a cross-sectional circle V, which is in a true circle shape, whose outer diameter dimension is D2, and which is orthogonal to an axis, it is not necessary that the measurement reference position $O_0$ on which three displacement detection axes intersect is a point on which the rotation center of the cylinder and the cross-sectional circle V intersect as mentioned above. In this case, since d2 among the components shown in the above-mentioned formula A is the distance from the circle center of the cross-sectional circle V to the surface of the cylinder, even if d2 is added to the above-described $\Delta S1$, this does not become to obtain the original LS1. Let this be LS1', and this includes difference between the distance from the surface of the cylinder on the detection axis of the sensor S1 to $O_0$, and d2. At the same time, similarly also in LS2' and LS3', when the cross-sectional circle V is in a true circle shape as mentioned above, the distances from $O_0$ to the surface of the cylinder is different every displacement detection axis. But, at the same time, it is possible to trace the floating point $O_n$ about the respective distances since the cross-sectional circle V is in a true circle shape, and a circumferential shape of the measured cross-section which is finally requested in the measurement of the measured cylinder 1 can keep similar relation to an actual one. Dimensional relation between the circumferential shape to the measured cross-section of the measured cylinder 1, which was obtained at this time, and an actual circumferential shape is equal to the relation between LS1 and LS1' which was described previously. Specifically, a distance between the starting point $O_0$ of the floating point in the measurement of the reference cylinder 2 on the detection axis of the sensor S1, and a mean center position of a locus on which the floating point $O_n$ moves as the cylinder 2 rotates in connection with the measurement is equivalent to the difference between the distance from the above-mentioned cylindrical surface to $O_n$, and d2. Hence, by obtaining this difference and correcting the measurement result, it is possible to make dimensions, which are given to the circumferential shape measured as a result, equivalent to what is based on d2.

Hence, since there is no need that an intersection of the detection axes of respective sensors coincides with the center of the cross-section of the above-described second cylinder, there is no need of high accuracy in manufacturing of a measurement machine, and the second cylinder may be bent with gravity.

In addition, since there is no need that the circle center of the cross-sectional circle V coincides with the intersection of the above-described respective displacement detection axes, there is no need that the reference cylinder 2 has high accuracy in positions other than the cross-sectional circle V. Hence, it is sufficient in production of the reference cylinder 2 only to perform such machining that obtains an independent circularity about only a part of an outer periphery of a cylinder. For example, when the outer diameter of the reference cylinder 2 is about 100 mm, it is possible enough to perform working with suppressing a circularity into 1 μm or less in a current technology level. Alternatively, since the above-described d2 is the distance from the center of the cross-sectional circle of the reference cylinder 2 to the circumference, when a shape of the cross-sectional circle is known even if it is not in a true circle shape, it is possible to use d2 (e.g., d2-1, d2-2, and d2-3) every detection axis of respective sensors for calculation beforehand.

In addition, an error which is expected to arise when rotating the measured cylinder 1 according to measurement, and is caused by a rotation angle will be referred to. Let a rotation error angle be θ°, let a distance between the circumference on the detection axis and the measurement reference position $O_0$ be $L_1$, and let a distance from the measurement reference position $O_0$ on an axis which intersects the detection axis with forming the above-mentioned rotation error angle with the measurement reference position $O_0$ to the circumference be $L_2$. Then, the error ΔL' given to the detection distance is given as the following formula:

$$\Delta L' = L_1 - L_2 \cdot \cos\theta$$

and hence, Δ' is very small. As an example, when a mean radius of a measuring object circle is 50 mm and 0.1° of rotation error arises, ΔL' is nearly 0.076 μm. This numerical value is $1.5 \times 10^{-4}$% to a measured value as an error. When taking into consideration that it is possible to expect that the reproducibility of stopping accuracy of a general and low-price rotating mechanism is about 0.04° sufficiently in addition to the measurement reproducibility of the above-mentioned ordinary displacement measuring instrument, it can be said that the influence of this error given to the measurement result is extremely small.

Subsequently, a circle central position and each radial distance in a position in orthogonal coordinate position are calculated from the obtained distances $L1_0$ to $L12_0$ using the known least-square center method. At this time, when adding the obtained twelve radial distances every distances in different directions every 180°, for example, $L1_0$ and $L7_0$, it is possible to obtain outer diameter values in respective directions.

Next, let the floating point $O_{n=0}$ be an origin (0, 0) in orthogonal coordinates, and positions of measuring points $1_0$ to $12_0$ on the circumference in the orthogonal coordinates will be obtained from distances $L1_0$ to $L12_0$. For the convenience of calculation, i is once substituted for n to be made an argument of the measuring points $1_0$ to $12_0$, and let components of the rectangular coordinate position be $x_i$ and $y_i$. They can be obtained by the following formulas:

$$x_i = L_1 \cdot \sin\{-\theta_1 \cdot (i-1)\}$$

$$y_i = L_1 \cdot \cos\{-\theta_1 \cdot (i-1)\}$$

In addition, a reason why $\theta_1$ is used as a negative angle in the above formula is because of expressing a position of each measuring point in the orthogonal coordinates in conformance to FIG. 3. Let the Y-axis of the rectangular coordinate system be 0°, and the angle is added sequentially counterclockwise.

Here, let a position of the true circle center O in the orthogonal coordinates be O (x, y), and it is possible $$x = \frac{2\sum x_i}{12}$$

$$y = \frac{2\sum y_i}{12}$$

to obtain them from the following formulas:

At this time, a number 12 given to denominators of both of left and right items is a number obtained by dividing 360° by $\theta_1$, that is, 30°, and this number changes with $\theta_1$.

Then, a roundness A will be obtained. With substituting the obtained O (x, y) for the origin (0, 0), let positions of the measuring points $1_0$ to $12_0$ on the circumference, which move with this, be $1_0'$ to $12_0'$. Then, components ($x_n$, $y_n$) of rectangular coordinate position are given from the following formulas:

$$X_n = X_i - x, \quad Y_n = Y_i - Y$$

True radial displacement amounts $L1_0'$ to $L12_0'$ are given from components ($x_n$, $y_n$) of the rectangular coordinate positions $1_0'$ to $12_0'$ which are obtained, with the following formulas:

$$L_n' = \sqrt{x_n^2 + y_n^2}$$

At this time, it is possible to obtain the roundness A of a cross-sectional circle orthogonal to a central axis as the difference between maximum and minimum values of $L1_0'$ to $L12_0'$.

The above measurement and calculation is performed for a desired cross-sectional circle, which is orthogonal to each central axis of the measured cylinder 1, and a circle center position and a radial displacement amount of each measured cross-sectional circle are obtained.

Next, a cylindricity of the measured cylinder 1 will be obtained.

A position of each intersection of a straight line connecting both circle centers of two cross-sectional circles, which are orthogonal to a central axis and are both ends of the measured cylinder 1, among the cross-sectional circles which are orthogonal to each measured central axis and are measured, and other cross-sectional circles orthogonal to respective central axes will be obtained by distance proportion. Then, a displacement amount on a straight line connecting each intersection, mentioned above, and each measuring point on a circumference is calculated as a radial distance using the method shown in formula 13. Here, it is possible to obtain the difference between maximum and minimum values of all the obtained distances as a cylindricity of the measured cylinder.

Since the measuring method described above is small in degrees of functions being influenced according to an outer diameter, an internal diameter, and a length of a measured cylinder, for example, in an outer diameter, it is possible to use this from a very thin object of about 5 mm to a thick object of several meters. Furthermore, there are many displacement detection means which can be used for this measuring method, and it is effective to use means of, for example, an electric micrometer, an eddy current type displacement detector, a laser displacement detector, a dial gauge, or the like. In addition, when there is a possibility of affecting measurement result because of generating elastic deformation such as bending in response to the influence of gravity during measurement because of the measured cylinder being too much thin to own length and weight, soft as a material, very thin, or the like, it is effective to perform measure by bringing the cylinder central axis of the measured cylinder closely to and in parallel to gravity or another external active direction.

In addition, in order to increase further the accuracy of a cylindricity to be finally obtained, it is preferable that a position of a cross-section orthogonal to a central axis of both ends is closer to the both end sections of a measured cylinder.

Here, when performing measurement by a plurality of rotations (a rotation here is an amount of rotation required for a rotation of one cross-section, that is, 360°) with changing a position in a cylinder axial direction like the above-mentioned measurement of a cylindricity, the accuracy of means of moving a sensor in parallel to a direction of a cylinder axis like the above-mentioned guide rails 4 generally becomes important. Nevertheless, in the case that a measured cylinder is placed and rotated using runner-like cylinder support jigs which are constructed of two pairs of two pieces respectively, totally four pieces for approximately both end portions of the measured cylinder, when rotational run-out of the runner-like cylinder support jigs is extremely small or a peripheral length of each runner is an integer-divided value of the peripheral length of the measured cylinder, the measured cylinder repeats the same rotation. Thus, even if a measured cylinder rotates two or more times, all the points of a cylindrical surface follow the always almost same locus every rotation. From this, even if a plurality of loci of the above-mentioned floating point are obtained when measurement is performed by a plurality of rotations with a position in a direction of a cylinder axis being changed like the measurement of a cylindricity, all the loci, or loci in a plurality of measurement positions to both support members with bounding intermediate support members in the direction of cylinder axes of the two pairs of runner-like cylinder support jigs which support the both ends of the above-mentioned measured cylinder form similar shapes which share a center position in a moving range. Hence, when arranging a plurality of cross-sectional circles, obtained by the measurement, with the above-mentioned center position as a common basis, it becomes possible to calculate and measure a cylindricity which is not affected by accuracy of moving means of a sensor like the above-mentioned guide rails 4 and deformation such as bending by gravity of the measured cylinder.

Furthermore, it is also effective in shortening of measuring time to perform measurement by a sensor for detecting a displacement without stopping rotation in each measurement position when rotating a measured cylinder in measurement of a circumferential shape of a cross-sectional circle orthogonal to each cylinder central axis.

Moreover, it is also very effective to perform measurement only in smaller times of rotations, and in particular, one rotation by measuring circumferential shapes of a plurality of cross-sectional circles orthogonal to the cylinder central axis simultaneously using a plurality of above-mentioned mounts which fix each sensor for detecting a displacement.

In addition, also when a measured cylinder is a hollow cylinder, and its inner periphery shape, and in particular, an inner diameter, or a surface displacement, circumferential run-out, and the like of an outer periphery on the basis of a center of the inner periphery are measured, it is possible to use the methods described above. In this case, when tracing a floating point with being equipped with three sensors in an outer periphery as mentioned above, since what is necessary is just to provide at least one displacement detection axis in an inner periphery, only one sensor is sufficient. Then, by giving correct positional relation by making this measure a sample such as a master having a known thickness beforehand, and performing correction by giving a detection result of the sensor in the inner periphery a moving state of the measured cylinder which was traced in the outer periphery, it is possible to grasp a circumferential shape of the inner periphery. At this time, it is most preferable to make a displacement detection axis of the sensor in the inner periphery coincide with the detection axis of the above-mentioned sensor S1 in the outer periphery, that is, to arrange it in a position of facing it. In this case, it is possible to measure the inner periphery by applying a thickness of the hollow cylinder on the basis of the above-mentioned positional relation to a measurement result of the outer periphery. In addition, even if arranging it in a direction other than it, it is possible to obtain a similar result by adding phase difference to the calculation.

Similarly, when a composite cylinder having a sub-cylinder(s) which projects to one side or both ends of a main cylinder to be measured is made a measured cylinder, it is also possible, for example, to measure a center of the main cylinder and to measure a surface displacement and circumferential run-out of the sub-cylinder(s) of the end portion(s) on the basis of this. As its method, similarly to the measuring method of an inner periphery which was described previously, when tracing a floating point with being equipped with three sensors for measuring the main cylinder, what is necessary is just to provide at least one displacement detection axis in a sub-cylinder. It is possible to grasp a circumferential shape of the sub-cylinder by performing correction by giving a detection result of the displacement detection axis of the sub-cylinder a moving state of the measured cylinder which was traced in the main cylinder measurement. When arranging the measurement results of the main cylinder and sub-cylinder with a machine reference or the above-mentioned central point of the locus of the above-mentioned floating point as a common reference, it is possible to measure the main cylinder and sub-cylinder of the composite cylinder as a common reference. Similarly, it is also possible to measure a center of the sub-cylinder in the end and to measure a surface displacement and circumferential run-out of the main cylinder on the basis of this. At this time, it is necessary to give positional relation between the sensor which measures the main cylinder, and the sensor which measures the sub-cylinder, and in particular, a distance in an axial direction of the measured cylinder and a distance in a direction orthogonal to the axis using a sample such as a master having a known dimension beforehand as positional relation to a measurement result.

Here, when the measured cylinder is supported by a plurality of support members and an outer diameter dimension every cylinder support member is different from others about a main cylinder portion, since a rotary axis of the measured cylinder is not parallel to that of the master, there is a possibility of disabling to calculate an outer diameter value of the sub-cylinder correctly. As for a general method about this correction method, it is possible to correct positional relation of the sensor in a sub-cylinder side with the sensor in a main cylinder side, and in particular, a distance in a direction orthogonal to the axis by distance-proportional calculation in the axial direction on the basis of difference between outer diameter values of the master in the cylinder support member and the measured cylinder, and difference of the above-mentioned distances in the axial direction. In addition, it is necessary to perform this correction in consideration of a supporting method of the cylinder support member. For example, when supporting both ends of the cylinder by two runners respectively, a sinking degree based on difference of the outer diameter value of the main cylinder changes with a pitch or runner outer diameters of two runners. Hence, correction of the sinking degree by a cylinder support method should be further added to the result (change degree) of the above-mentioned distance-proportional calculation.

Although the present invention will be explained below specifically using examples, the present invention is not limited by such examples.

EXAMPLE 1

Ten A3003 aluminum pipes which had been given machining beforehand as a measured cylinder, and which had a machining set outer diameter of 84.0 mm, an inner diameter of 78.0 mm, and a length of 360.0 mm were prepared, and were named Sample No. 1 to Sample No. 10.

Figure 9:
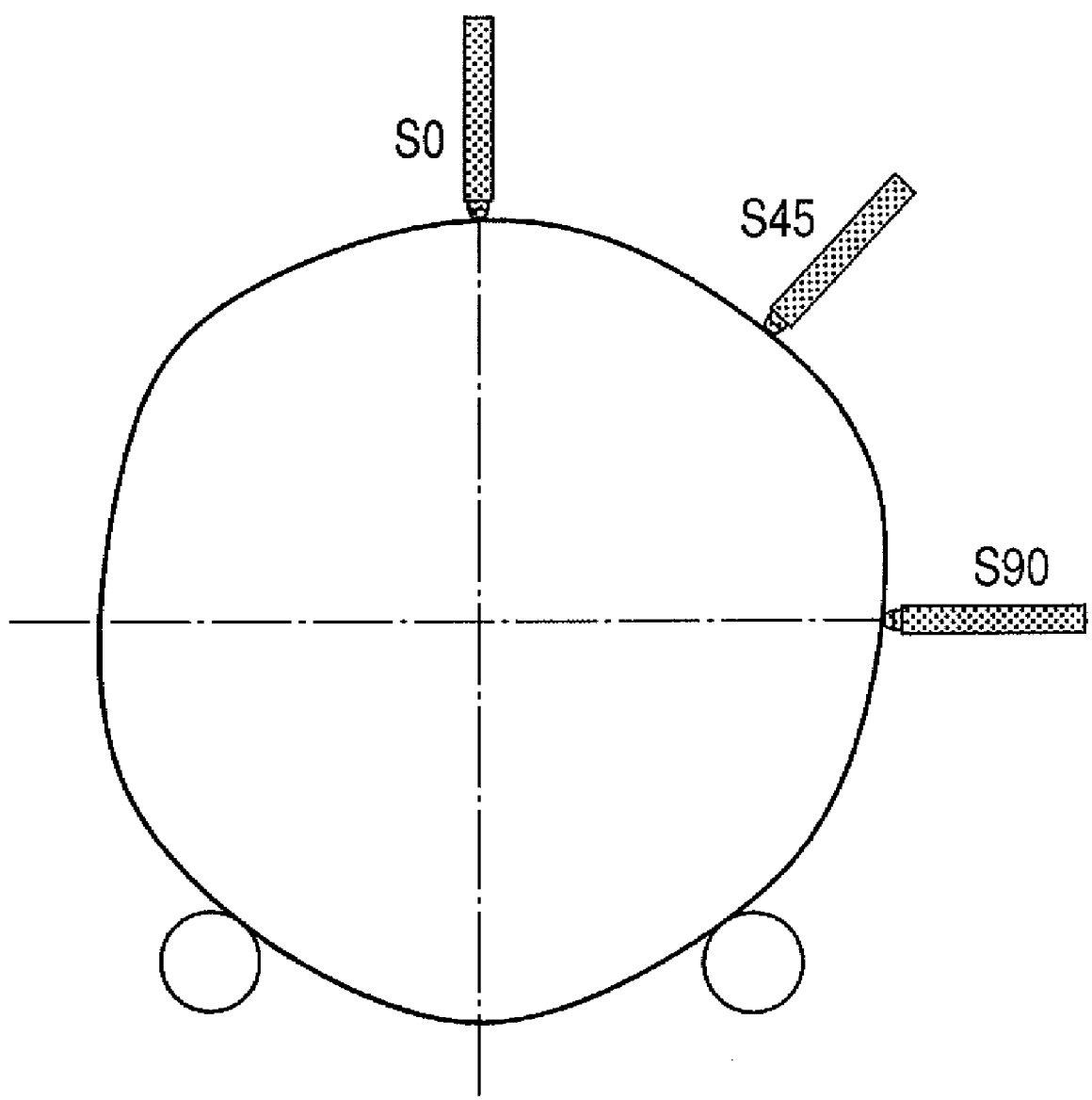
FIG. 9 is a diagram showing positions of the sensors for detecting displacements in example 1.

The measured cylinder Sample No. 1 was placed on a cylinder support jig of a cylinder measuring instrument where, as shown in FIG. 9, three sensors S0, S45 and S90 for detecting displacements were arranged in a shape formed by connecting a measurement reference point and said three sensors being a fan shape with measurement axes of respective sensors for detecting displacements intersecting with each other at a predetermined point within a cross-sectional circle orthogonal to an axis of the cylinder, and with forming an angle of 45° with adjacent one of the sensors with the point as a center. The above-mentioned three sensors for detecting displacements were arranged apart 80 mm from an end of the measured cylinder in a central axis direction of the cylinder, and each sensor for detecting a displacement used was an MCH335 electric micrometer made by Mitutoyo Co., Ltd. Then, measurement was performed totally 8 times with the above-mentioned rotation drive transfer machine by rotating the cylinder by 45° every measurement. In addition, a distance from the intersection of the above-mentioned detection axes to each sensor for detecting a displacement had been measured beforehand, and a measured value of the sensor for detecting a displacement in this embodiment is shown as a value measured a distance from the intersection point of respective detection axes to an intersection point of a cylindrical surface on the same cross-section orthogonal to a rotation axis of the measured cylinder and each of the above-mentioned detection axes.

The measured cylinder was rotated at 6 revolutions per minute when measuring. Measurement was performed with defining that the time which the measurement took at this time was the time required from placing the measured cylinder on the above-mentioned cylinder support jig to completing one rotation of the measured cylinder for measurement.

Hereinafter, in tables in drawings used in the first example, measurement in S0 position at the time of measurement start is set to 0°, and 45° is added by turns to a position on the circumferential surface which arrives S0 according to a rotation of the measured cylinder.

In order to obtain a moving distance of the above-mentioned floating point, each moving distance on the detection axes of the sensors for detecting displacements S45 and S90 is calculated using the above-mentioned formulas 1 and 2. At this time, a moving distance on each axis is calculated as difference between a measured value of S45 and a measured value of S0 before 45° of rotation on the detection axis of S45, and difference between a measured value of S90 and a measured value of S45 before 45° of rotation on the detection axis of S90, respectively.

Next, using the above-mentioned formula 13, $\Delta x$ in a rectangular coordinate position was obtained, and $\Delta y$ was calculated next, using the above-mentioned formula 12. Here, $\Delta x$ and $\Delta y$ are moving distances of the floating point $O_n$ shown in a rectangular coordinate position. Then, a true value of an S0 position, that is, a distance to a measured cylinder surface on the basis of the floating point $O_n$ was calculated by subtracting this $\Delta y$ from the measured value of S0.

Next, a distance to each point on the basis of the floating point $O_n$ was converted into a rectangular coordinate position. Using $X_n$ and $Y_n$ obtained in this way, a true circle center coordinates O (x, y) were obtained by the above-mentioned least-square circle center method, and a center X coordinate and a center Y coordinate were obtained.

Then, distances of the X axial component and Y axial component from the obtained center coordinate position to each point, a direct distance to each point, that is, a radial distance of each true point, and further, a roundness was obtained from the difference of a maximum value and a minimum value of them.

About the above, Sample No. 2 to Sample No. 10 were measured similarly, and the above-mentioned durations and roundnesses were obtained.

FIGS. 10 and 11 show data from measured values of each of the above-mentioned sensors for detecting displacements to the above-mentioned circle center coordinate positions among data obtained by the above measurement. Then, FIGS. 12 and 13 show distances of the X axial component and Y axial component from the above-mentioned center coordinate position to each point, distances to each point, and maximum and minimum values of them.

COMPARATIVE EXAMPLE 1

Each outer surface roundness at a position apart 80 mm from the lower edge at the time of placement of the measured cylinder in a direction of the cylinder central axis was measured for the aluminum pipes Sample No. 1 to Sample No. 10 measured in the first example using a roundness measuring instrument (trade name: round test RA-H5000AH, made by Mitutoyo Co., Ltd.). Each duration for measurement was measured as the time required from placing the measured cylinder on a rotary table to completing a series of programs which continuously ran for automatic centering, automatic leveling, and automatic measurement.

In addition, as for the above-mentioned automatic centering and an automatic leveling steps, an automatic and high-speed mode was adopted, a centering position was set at 20 mm from a lower edge of the measured cylinder, a leveling position was set at 80 mm from the above-mentioned lower edge, a magnification was set at 5000×, an area was set at 8 μm, and the rotating speed of the rotary table was set at 10 rpm. Then, the automatic centering, automatic leveling, and roundness measurement were implemented. In addition, when placing the measured cylinder on the above-mentioned rotary table, the measured cylinder was directly placed without using a three-claw chuck, made by the company, and other fixtures in consideration of shortening of the measurement time. In addition, in order to delete the increase of the above-mentioned duration arising from a plurality of operation of the automatic centering and automatic leveling, data of measurement which required two or more times of automatic centering or automatic leveling was not adopted as data, measurement was retried until the measurement which required only one operation of automatic centering or automatic leveling was achieved, and this data was adopted as the data of the duration.

(Evaluation)

Figures 14, 15:
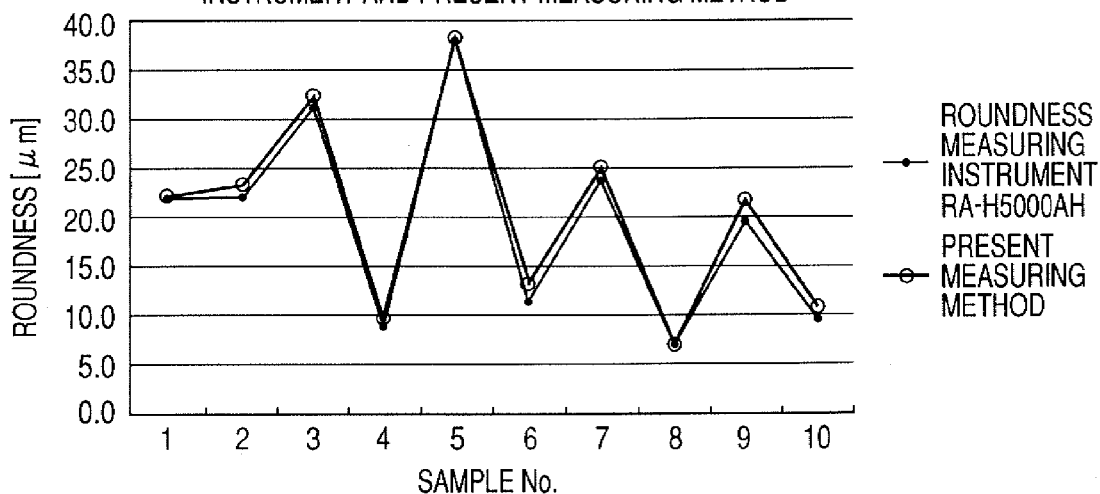
FIG. 14 shows roundness obtained in example 1 and a first comparative example.
FIG. 15 is a graph of comparing roundness obtained in example 1 and first comparative example.

FIGS. 14 and 15 show a value of each roundness and each difference measured in the first example and first comparative example. In addition, FIG. 16 shows each duration measured in the first example and first comparative example.

From FIGS. 14 and 15, the difference between the measurement results by respective measuring methods, that is, the first example and first comparative example is 2.2 μm at the maximum, and hence, it can be judged that it is sufficiently small.

In addition, from FIG. 16, it is possible to confirm that a measurement duration of the first example is shortened by 54.7% to a measurement duration of the first comparative example.

EXAMPLE 2

An A3003 aluminum pipe which had been given machining beforehand as a measured cylinder, and which had a machining set outer diameter of 80.0 mm, an inner diameter of 74.0 mm, and a length of 360.0 mm was prepared.

Figure 17:
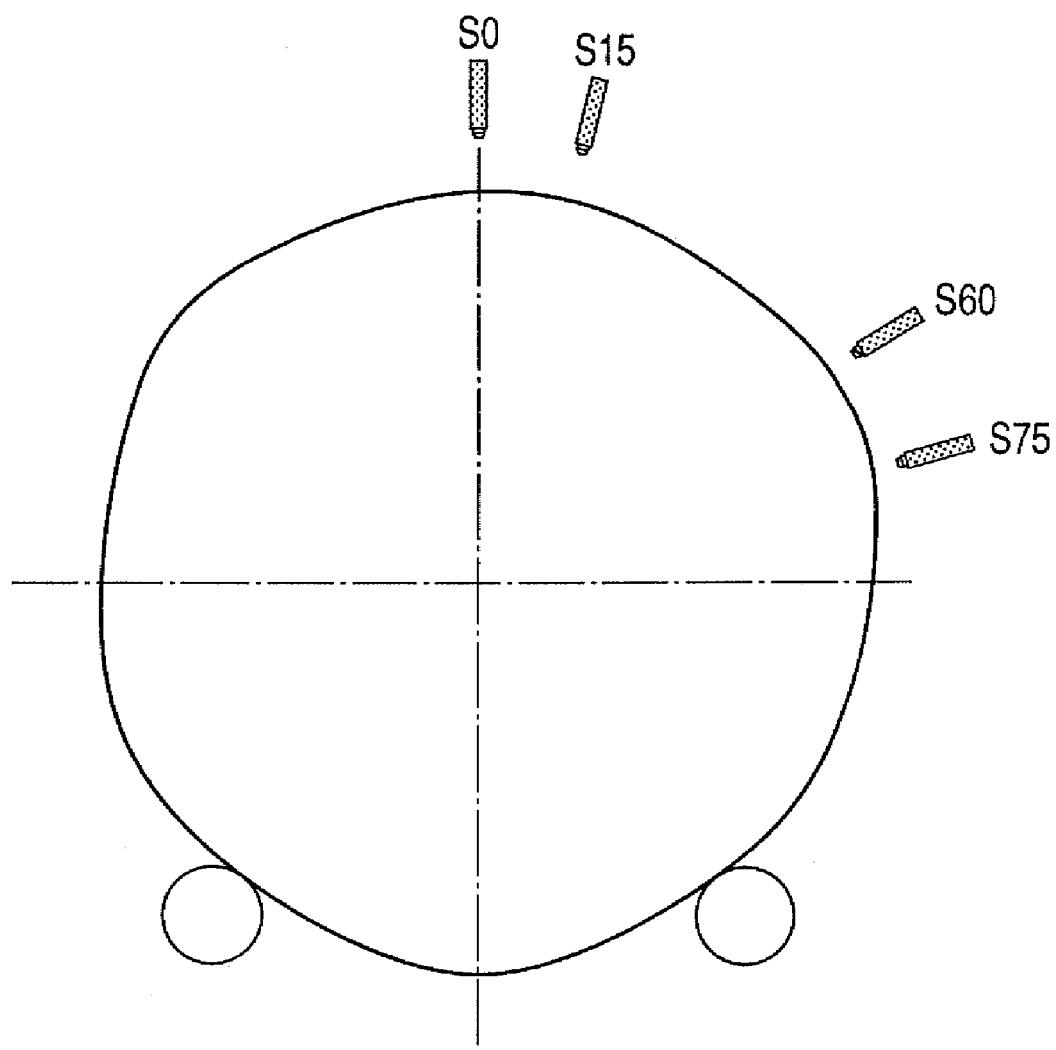
FIG. 17 is a schematic diagram showing positions of sensors for detecting displacements in example 2.

This measured cylinder was placed on the cylinder support jig of the same cylinder measuring instrument as that in FIG. 2. Sensors S0, S15, and S60 and S75 for detecting displacements were arranged on a mount, which is shown in FIG. 17, so that the sensors for detecting displacements might be located on the same cross-section, which was orthogonal to a rotation axis and was apart 30 mm from an end of the measured cylinder in a direction of a cylinder central axis, and might be oriented to an intersect point of the rotation axis of the measured cylinder and the cross-section orthogonal to the rotation axis, with the above-mentioned intersection point as a center, and with forming an angle of 15° with one another, respectively. Furthermore, S0 and S60 were arranged so that they might form an angle of 60°. As each sensor for detecting a displacement, an eddy current type sensor for detecting a displacement made by KAMAN Corp. was used, and a position of each sensor for detecting a displacement was adjusted so that each distance from the above-mentioned intersection point might become equal. Then, measurement was performed totally 24 times with the above-mentioned rotation drive transfer machine by rotating the cylinder by 15° every measurement. A displacement amount between each sensor for detecting a displacement and a surface of the measured cylinder was measured as a distance. Hereinafter, in tables in drawings used in the second and third examples, measurement in an S0 position at the time of measurement start is set to 0°, and 15° is added by turns to a position on the circumferential surface which arrives S0 according to a rotation of the measured cylinder. This is shown in FIG. 18.

Next, in order to regard each measured value as a differential value for convenience of calculation, let a first measured value, that is, a measured value of the sensor S0 for detecting a displacement at the time of the measured cylinder not rotating once be 0, and all the other measurement results are calculated as differentials between with S0. In addition, in order to perform subsequent calculation smoothly, all the differential values are converted into positive numbers. In this example, all the differential values were subtracted from 50 μm which was an arbitrary constant to be made positive numerical values. This is shown in FIG. 19.

Next, in order to obtain a moving distance of the above-mentioned floating point, each moving distance on the detection axes of the sensors S15 and S75 for detecting displacements is calculated using the above-mentioned formula (2). At this time, the moving distance on each axis is calculated as difference between a measured value of S15 and a measured value of S0 before 15° of rotation on the detection axis of S15, and difference between a measured value of S75 and a measured value of S60 before 15° of rotation on the detection axis of S75, respectively.

Δx in a rectangular coordinate position was obtained from the obtained moving distances on the two axes using a term b among the formulas shown in the above-mentioned formula 12, and Δy was calculated next, using a term of $\Delta 2_1$ shown in the above-mentioned formula 12. Then, a true value of an S0 position, that is, a displacement amount of a surface of the measured cylinder 1 on the basis of the floating point $O_n$ was obtained by subtracting this Δy from the measured value of S0. Hereinafter, residual measurements of the measured cylinder to one-round measurement were performed similarly. This is shown in FIG. 20.

Next, the true center of a circle will be obtained.

The displacement amounts of respective points on the basis of the floating point $O_n$ which had been obtained in FIG. 20 were converted into rectangular coordinate components. Then, using $X_n$ and $Y_n$ obtained in this way, a true circle center coordinates O (x, y) were obtained by the above-mentioned least-square circle center method, and (−4.5, −0.5) was obtained. In addition, 6.1 Δm was obtained as the roundness by obtaining the displacement amounts of X axial component and Y axial component in each point on the basis of the floating point $O_n$, the true displacement amount in the radial direction to each point, and the difference between a maximum value (53.3 μm) and a minimum value (47.2 μm) of them. This is shown in FIG. 21.

EXAMPLE 3

An A3003 aluminum pipe which had been given general machining beforehand as a first measured cylinder, and which had a machining set outer diameter of 84.0 mm, an inner diameter of 78.0 mm, and a length of 360.0 mm was prepared, and this is made a measured cylinder sample.

Simultaneously, a second cylinder which was prepared was an aluminum pipe which was the same as the first cylinder except a circularity in a position of 80 mm in a direction of a cylinder central axis from one end of the cylinder being 0.20 μm and a mean outside diameter value being 84.000 mm. In addition, in the measurement of the roundness of the outer surface of the second cylinder, a circularity-measuring instrument (trade name: Round test RA-H5000AH, made by Mitutoyo Co., Ltd.) was used.

Figure 22:
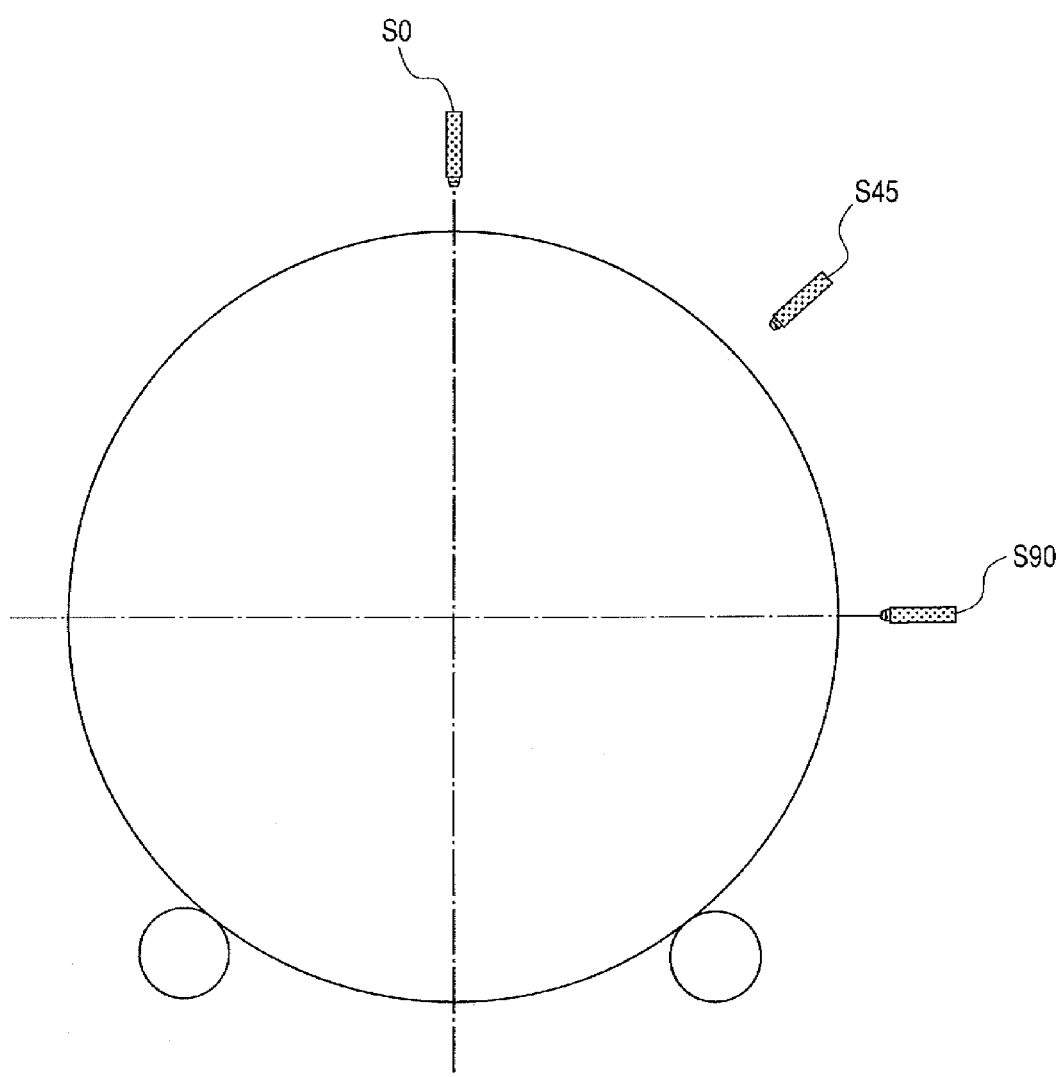
FIG. 22 is a diagram showing sensor positions for detecting displacements in example 3.
Figure 26:
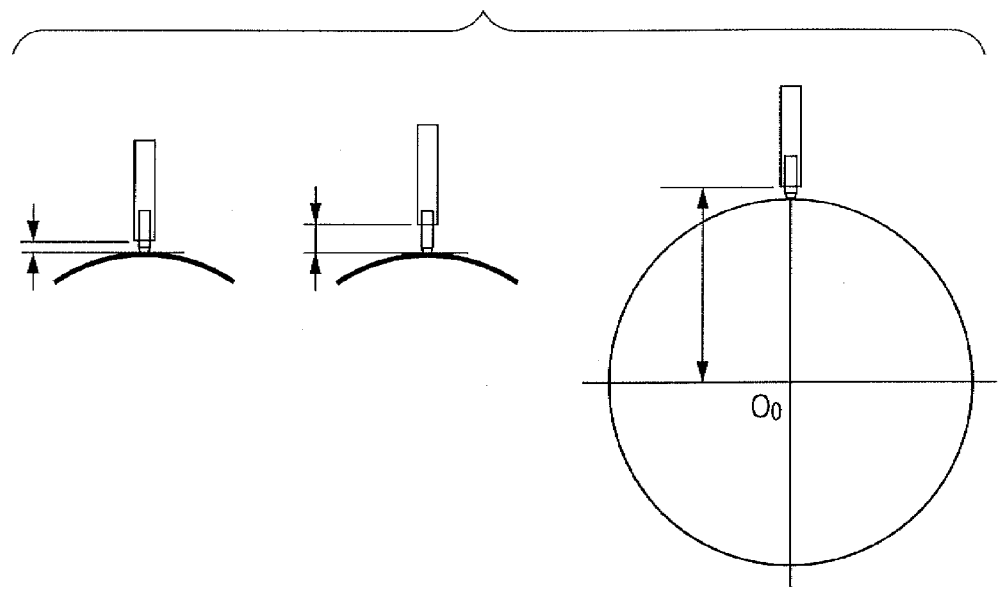
FIG. 26 shows measured distances of a stylus type sensor.
Figure 27:
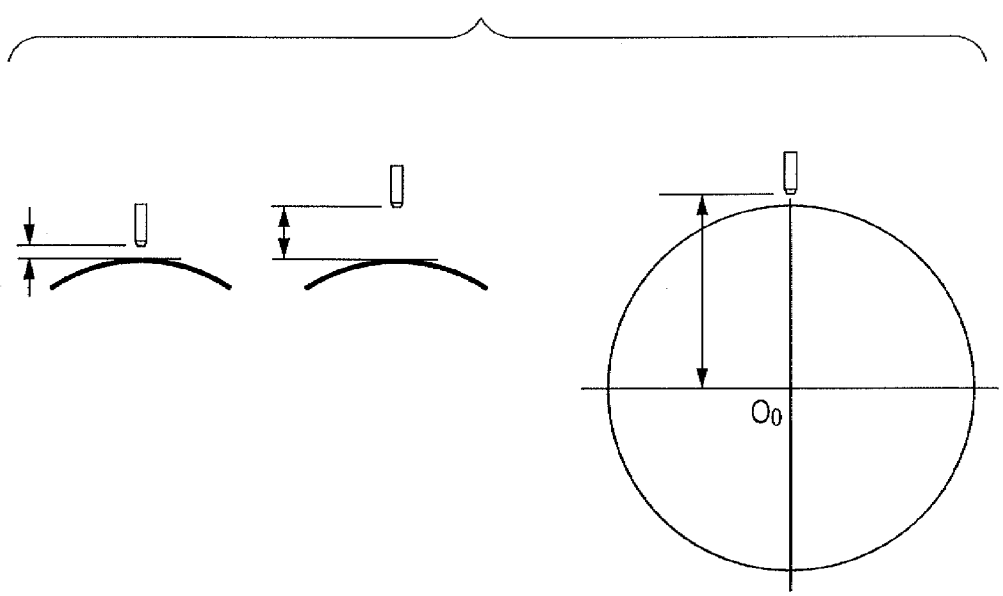
FIG. 27 shows measured distances of an eddy current type sensor.

The second cylinder was placed on cylinder support jigs of a cylindrical body measuring instrument where, as shown in FIG. 22, three sensors for detecting a displacement S0, S45 and S90 were arranged in a shape, formed by connecting a measurement reference point ($O_0$) and the three sensors being a fan shape, with measurement axes of respective sensors approximately intersecting with each other at a predetermined point within a cross-sectional circle in a direction orthogonal to an axis of the cylinder, and with forming an included angle of 45° mutually with the point as a center. The above-mentioned three sensors were arranged in a position 80 mm apart in a direction of the central axis of the cylinder from one end of the measured cylinder, and the sensors used were eddy current type sensors made by KAMAN Corp. The detection values of respective sensors at this time were as follows:

ΔS0=448 μm, ΔS45=273 μm, and ΔS90=296 μm

When obtaining a distance from each sensor to the above-mentioned measurement reference position $O_0$ using the above-mentioned formula A every sensor at this time, that results were as follows.

LS0=42.448 mm, LS45=42.273 mm, and LS90=42.296 mm

Next, the second cylinder on the support jigs was exchanged for the above-described first cylinder as a measured cylinder, and measurement was performed totally 8 times with a rotation drive transfer machine by rotating the cylinder by 45° every measurement. Then, the obtained detection values, ΔS0, ΔS45, and ΔS90 were subtracted from the above-mentioned LS0, LS45, and LS90 every sensor, and distances from each measurement point to the measurement reference position $O_0$ were obtained. These are shown in FIG. 23.

Hereinafter, in tables of drawings used in the third example, measurement in an S0 position at the time of measurement start is set to 0°, and 45° is added by turns to a measured position on the circumferential surface which arrives S0 according to a rotation of the measured cylinder.

In order to obtain a moving distance of the above-mentioned floating point, each moving distance on the detection axes of the sensors S45 and S90 is calculated using the above-mentioned formulas (1) and (2). At this time, the moving distance on each axis is calculated as difference between a measured value of S45 and a measured value of S0 before 45° of rotation on the detection axis of S45, and difference between a measured value of S90 and a measured value of S45 before 45° of rotation on the detection axis of S90, respectively.

Next, using the above-mentioned formula 13, Δx in an orthogonal coordinate position was obtained, and Δy was calculated next, using the above-mentioned formula 12. Here, Δx and Δy are moving distances of the floating point $O_n$ shown in an orthogonal coordinate position. Then, a true value of the S0 position, that is, a distance to a measured cylinder surface on the basis of the floating point $O_n$ was calculated by subtracting this Δy from the measured value of S0.

Next, a distance to each point on the basis of the floating point $O_n$ was converted into an orthogonal coordinate position. Using $X_n$ and $Y_n$ obtained in this way, a true circle center coordinates O (x, y) were obtained by the above-mentioned least-square center method, and a center X coordinate and a center Y coordinate were obtained.

Then, distances of the X axial component and Y axial component from the obtained center coordinate position to each point, a direct distance to each point, that is, a true radial distance of each point, a circularity was obtained from difference between a maximum value and a minimum value of them, and further, outer diameter values in the positions of 0 to 180° and 90 to 270° were obtained.

FIG. 24 shows data from measured values of each of the above-mentioned sensors S0, S45, and S90 to the above-mentioned circle center coordinate positions among data obtained by the above measurement. Then, FIG. 25 shows distances of the X axial component and Y axial component from the above-mentioned center coordinate position to each point, distances to each point, maximum and minimum values of them, circularities, and outer diameter values. In addition, all the dimensional units in FIGS. 23 to 25 were described in mm.

EXAMPLE 4

An A3003 aluminum pipe which had been given general machining beforehand as a first measured cylinder, and which had a machining set outer diameter of 84.0 mm, an inner diameter of 78.0 mm, and a length of 360.0 mm was prepared, and this was made a measured cylinder sample. In addition, a second cylinder which was prepared was an aluminum pipe which was the same as the first cylinder except a circularity in a position of 80 mm in a direction of a cylinder central axis from one end of the cylinder being sufficiently small, for example, 0.50 μm and a mean outside diameter value being 84.000 mm. In addition, the measurement of the second cylinder was performed using a circularity-measuring instrument (trade name: Round test RA-H5000AH, made by Mitutoyo Co., Ltd.).

The second cylinder was placed on cylinder support jigs of a cylindrical measuring instrument as shown in FIG. 17, and as for sensors S0, S15, S60, and S75 for detecting displacements, measurement axes of respective sensors approximately intersect with each other at a predetermined point within a cross-sectional circle in a direction orthogonal to an axis of the cylinder, and S0 and S15, and S60 and S75 were arranged in a shape, formed by connecting a measurement reference point ($O_0$) and the three sensors being a fan shape, with forming an included angle of 15° mutually with the predetermined point as a center. Furthermore, S0 and S60 were arranged so that they might form an included angle of 60°. As the sensors for detecting displacement, it was possible to use the eddy current type sensors made by KAMAN Corp.

Then, similarly to the third example, after measuring distances from each sensor S0, S15, S60, and S75 to the second cylinder, distances from each sensor to the above-mentioned measurement reference position $O_0$ were obtained using the above-mentioned formula A every sensor, and LS0, LS15, LS60, and LS75 were obtained.

Next, the second cylinder on the support jigs was exchanged for the above-described first cylinder as a measured cylinder, and measurement was performed totally 24 times with a rotation drive transfer machine by rotating the cylinder by 15° every measurement. Then, the obtained detection values were subtracted from the above-mentioned LS0, LS15, LS60, and LS75 every sensor, and distances from each measurement point to the measurement reference position $O_0$ were obtained.

Hereafter, similarly to the second example, a circumferential shape and a circularity of the cross-sectional circle of the first cylinder were obtained.

EXAMPLE 5

Let 20 cross-sectional circles, which were apart 30 mm, 35 mm, 40 mm, 60 mm, 80 mm, 90 mm, 120 mm, 140 mm, 150 mm, 180 mm, 200 mm, 210 mm, 240 mm, 260 mm, 270 mm, 300 mm, 310 mm, 320 mm, 330 mm, and 350 mm from one end of the measured cylinder 1 toward another end and were orthogonal to a cylinder central axis, be measured circles. Then, using the instrument described in the second example, measurements at 24 points totally every 15° per one-round measurement were performed to these, respectively, and the distance between each sensor S0, S15, S60, and S75 for detecting a displacement and the surface of the measured cylinder was obtained.

Next, after the measured values being made positive differential values using the same method as that in the second example, displacement amounts of a surface of a measured cylinder on the basis of the floating point $O_n$ of each measured circle were obtained similarly to the second example.

Next, similarly to the second example, X and Y axial components of a displacement amount of each point on the basis of the center coordinates of each measured circle, that is, the floating point $O_n$, a maximum value and a minimum value of each circle, and a roundness by these were obtained.

Then, what were obtained were positions of intersections of a straight line connecting both circle centers of two measured circles, located in both ends among the 20 measured circles which were measured, that is, the circle at the 30 mm position in the direction of the cylinder central axis and the circle at the 350 mm position, and other measured circles by the distance proportion. Next, a displacement amount as x and y coordinate components of each measuring point on the circumference on the basis of the above-mentioned each intersection was calculated every measured circle. Furthermore, a radial displacement amount of each measuring point on the circumference on the basis of the above-mentioned each intersection was calculated from the displacement amount as the above-mentioned each coordinate component. This is shown in FIG. 28. Here, 9.0 μm of cylindricity of the measured cylinder was obtained with the difference of a maximum value (54.5 μm) and a minimum value (45.5 μm) of all the obtained distances.

This application claims the benefit of Japanese Patent Application No. 2004-254363, filed Sep. 1, 2004, Japanese Patent Application No. 2005-254327, filed Sep. 2, 2005, Japanese Patent Application No. 2006-052880 filed Feb. 28, 2006, and PCT International Application No. PCT/JP2006/304200, filed Feb. 28, 2006, which are hereby incorporated by reference herein in their entirety.

What is claimed is:

1. A measuring method of a shape of a cross-sectional circle, which is orthogonal to an axis of a cylinder to be measured, by the following steps (i) to (vi) using measuring means constructed of
   (a) a cylinder support jig, and
   (b) a mount having first, second and third sensors for detecting displacements, which are located on a cross section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the second sensor and the third sensor are θ°, comprising:
   (i) a step of measuring each of distances $\Delta L1$, $\Delta L2$ and $\Delta L3$ between each of the first, second and third sensors and intersecting points of lines connecting the respective sensors and the $O_0$ with a circumference of the cross-sectional circle of the cylinder to be measured,
   (ii) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$L1=LS1-\Delta L1$, $L2=LS2-\Delta L2$, $L3=LS3-\Delta L3$, wherein LS1, LS2 and LS3 are distances between each of the first, second and third sensors and the $O_0$,
   (iii) a step of rotating the cylinder to be measured by θ° in a direction toward the second sensor from the first sensor, and repeating the steps (i) and (ii),
   (iv) a step of calculating a distance $\Delta 01$ between a floating point 0', which is a point on the cross-sectional circle of the cylinder to be measured corresponding to the $O_0$ before the rotation in the step (iii), and a line passing through the $O_0$ and intersecting at a right-angle with the line connecting the first sensor and the $O_0$, from L1 and L2 obtained in the step (ii) and L2 and L3 obtained in the step (iii),
   (v) a step of calculating a distance between the 0' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and $\Delta 01$ obtained in the step (iv), and
   (vi) a step of obtaining the shape of the cross-sectional circle based on the distance calculated in the step (v).

2. A measuring method of a shape of a cross-sectional circle, which is orthogonal to an axis of a cylinder to be measured, according to claim 1, further comprising the following step (vii):
   (vii) a step of repeating once or two or more times the steps (i) to (v), and obtaining the distance between the 0' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (iii).

3. A measuring method of a shape of a cross-sectional circle, which is orthogonal to an axis of a cylinder to be measured, by the following steps (i) to (vi) using measuring means constructed of
   (a) a cylinder support jig, and
   (b) a mount having first, second, third and fourth sensors for detecting displacements, which are located on a cross-section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the third sensor and the fourth sensor are $\theta°$, comprising:

(i) a step of measuring each of distances $\Delta L1$, $\Delta L2$, $\Delta L3$ and $\Delta L4$ between each of the first, second, third and fourth sensors and intersecting points of lines connecting the respective sensors and the $O_0$ with a circumference of the cross-sectional circle of the cylinder to be measured, (ii) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, $L4 = LS4 - \Delta L4$, wherein LS1, LS2, LS3 and LS4 are distances between each of the first, second, third and fourth sensors and the $O_0$, (iii) a step of rotating the cylinder to be measured by $\theta°$ in a direction toward the second sensor from the first sensor, and repeating the steps (i) and (ii), (iv) a step of calculating a distance $\Delta O1$ between a floating point $0'$, which is a point on the cross-sectional circle of the cylinder to be measured corresponding to the $O_0$ before the rotation in the step (iii), and a line passing through the $O_0$ and intersecting at a right-angle with the line connecting the first sensor and the $O_0$, from L1 and L3 obtained in the step (ii) and L2 and L4 obtained in the step (iii), (v) a step of calculating a distance between the $0'$ and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and $\Delta O1$ obtained in the step (iv), and (vi) a step of obtaining the shape of the cross-sectional circle based on the distance calculated in the step (v).

4. A measuring method of a shape of a cross-sectional circle, which is orthogonal to an axis of a cylinder to be measured, according to claim 3, further comprising the following step (vii):

(vii) a step of repeating once or two or more times the steps (i) to (v), and obtaining the distance between the $0'$ and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (iii).

5. A method for determining a shape of a cross-sectional circle, which is orthogonal to an axis of a cylinder to be measured, by the following steps (i) to (viii) using measuring means constructed of (a) a cylinder support jig, and (b) a mount having first, second and third sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the second sensor and the third sensor are $\theta°$, the cross-sectional circle of the reference cylinder being a true circle having a radius of d2, comprising:

(i) a step of measuring each of distances $\Delta LR1$, $\Delta LR2$ and $\Delta LR3$ between each of the first, second and third sensors and intersecting points of lines connecting the respective sensors and the $O_0$ with a circumference of the cross-sectional circle of the reference cylinder, (ii) a step of calculating each of distances LS1, LS2 and LS3 between each of the first, second and third sensors and the $O_0$ according to the following equations:

$LS1 = d2 + \Delta LR1$, $LS2 = d2 + \Delta LR2$, $LS3 = d2 + \Delta LR3$, (iii) a step of measuring each of distances $\Delta L1$, $\Delta L2$ and $\Delta L3$ between each of the first, second and third sensors and intersecting points of lines connecting the respective sensors and the $O_0$ with a circumference of the cross-sectional circle of the cylinder to be measured, (iv) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, (v) a step of rotating the cylinder to be measured by $\theta°$ in a direction toward the second sensor from the first sensor, and repeating the steps (iii) and (iv), (vi) a step of calculating a distance $\Delta O1$ between a floating point $0'$, which is a point on the cross-sectional circle of the cylinder to be measured corresponding to the $O_0$ before the rotation in the step (v), and a line passing through the $O_0$ and intersecting at a right-angle with the line connecting the first sensor and the $O_0$, from L1 and L2 obtained in the step (iv) and L2 and L3 obtained in the step (v), (vii) a step of calculating a distance between the $0'$ and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and $\Delta O1$ obtained in the step (vi), and (viii) a step of obtaining the shape of the cross-sectional circle based on the distance calculated in the step (vii).

6. A measuring method of a shape of a cross-sectional circle, which is orthogonal to an axis of a cylinder to be measured, according to claim 5, further comprising the following step (ix):

(xi) a step of repeating once or two or more times the steps (iii) to (vii), and obtaining the distance between the 0' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (v).

7. A method for determining a shape of a cross-sectional circle, which is orthogonal to an axis of a cylinder to be measured, by the following steps (i) to (viii) using measuring means constructed of (a) a cylinder support jig, and
(b) a mount having first, second, third and fourth sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the third sensor and the fourth sensor are θ°, the cross-sectional circle of the reference cylinder being a true circle having a radius of d2, comprising:

(i) a step of measuring each of distances ΔLR1, ΔLR2, ΔLR3 and ΔLR4 between each of the first, second, third and fourth sensors and intersecting points of lines connecting the respective sensors and the $O_0$ with a circumference of the cross-sectional circle of the reference cylinder, (ii) a step of calculating each of distances LS1, LS2, LS3 and LS4 between each of the first, second, third and fourth sensors and the $O_0$ according to the following equations:

$LS1 = d2 + \Delta LR1$, $LS2 = d2 + \Delta LR2$, $LS3 = d2 + \Delta LR3$, $LS4 = d2 + \Delta LR4$, (iii) a step of measuring each of distances ΔL1, ΔL2, ΔL3 and ΔL4 between each of the first, second, third and fourth sensors and intersecting points of lines connecting the respective sensors and the $O_0$ with a circumference of the cross-sectional circle of the cylinder to be measured, (iv) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, $L4 = LS4 - \Delta L4$, (v) a step of rotating the cylinder to be measured by θ° in a direction toward the second sensor from the first sensor, and repeating the steps (iii) and (iv), (vi) a step of calculating a distance Δ01 between a floating point 0', which is a point on the cross-sectional circle of the cylinder to be measured corresponding to the $O_0$ before the rotation in the step (v), and a line passing through the $O_0$ and intersecting at a right-angle with the line connecting the first sensor and the $O_0$, from L1 and L3 obtained in the step (iv) and L2 and L4 obtained in the step (v), (vii) a step of calculating a distance between the 0' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and Δ01 obtained in the step (vi), and (viii) a step of obtaining the shape of the cross-sectional circle. based on the distance calculated in the (vii).

8. A measuring method of a shape of a cross-sectional circle, which is orthogonal to an axis of a cylinder to be measured, according to claim 7, further comprising the following step (ix):

(ix) a step of repeating once or two or more times the steps (iii) to (vii), and obtaining the distance between the 0' and a line intersecting at right angles with a line connecting the sensor S1 and the $O_0$, at an intersecting point of the line connecting the sensor S1 and the $O_0$ with a circumference of a cross-section of the cylinder to be measured after the rotation for each rotation in the step (v).

9. A measuring method of a cylindrical shape of a cylinder to be measured by the following steps (I) to (III), comprising:

(I) a step of measuring shapes of a plurality of cross-sectional circles, which are orthogonal to an axis of the cylinder,
(II) a step of measuring the cylindrical shape of the cylinder from the shapes of the plurality of cross-sectional circles measured in the step (I),
(III) a step of obtaining the shape of the cylinder measured in the step (II), wherein measurements of shapes of the plurality of cross-sectional circles in the step (I), are carried out respectively by the following steps (i) to (vi) using measuring means constructed of (a) a cylinder support jig, and
(b) a mount having first, second and third sensors for detecting displacements, which are located on a cross-section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the second sensor and the third sensor are $\theta°$, and comprise:

(i) a step of measuring each of distances $\Delta L1$, $\Delta L2$ and $\Delta L3$ between each of the first, second and third sensors and intersecting points of lines connecting the respective sensors and the $O_0$ with a circumference of the cross-sectional circle of the cylinder to be measured, (ii) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, wherein LS1, LS2 and LS3 are distances between each of the first, second and third sensors and the $O_0$, (iii) a step of rotating the cylinder to be measured by $\theta°$ in a direction toward the second sensor from the first sensor, and repeating the steps (i) and (ii), (iv) a step of calculating a distance $\Delta O1$ between a floating point O', which is a point on the cross-sectional circle of the cylinder to be measured corresponding to the $O_0$ before the rotation in the step (iii), and a line passing through the $O_0$ and intersecting at a right-angle with the line connecting the first sensor and the $O_0$, from L1 and L2 obtained in the step (ii) and L2 and L3 obtained in the step (iii), (v) a step of calculating a distance between the O' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and $\Delta O1$ obtained in the step (iv), and (vi) a step of obtaining the shape of the cross-sectional circle based on the distance calculated in the step (v).

10. A measuring method of a cylindrical shape of a cylinder to be measured by the following steps (I) to (III) comprising:

(I) a step of measuring shapes of a plurality of cross-sectional circles, which are orthogonal to an axis of the cylinder, (II) a step of measuring the cylindrical shape of the cylinder from the shapes of the plurality of cross-sectional circles measured in the step (I), (II) a step of obtaining the shape of the cylinder measured in the step (II), wherein measurements of shapes of the plurality of cross-sectional circles in the step (I), are carried out respectively by the following steps (i) to (vi) using measuring means constructed of (a) a cylinder support jig, and (b) a mount having first, second, third and fourth sensors for detecting displacements, which are located on a cross-section including the cross-sectional circle, are aimed at a measurement reference point ($O_0$) which is an intersecting point of the axis with the cross-sectional circle, and are arranged and fixed so that an angle formed between lines connecting the $O_0$ with the first sensor and the second sensor and an angle formed between lines connecting the $O_0$ with the third sensor and the fourth sensor are $\theta°$, and comprise:

(i) a step of measuring each of distances $\Delta L1$, $\Delta L2$, $\Delta L3$ and $\Delta L4$ between each of the first, second, third and fourth sensors and intersecting points of lines connecting the respective sensors and the $O_0$ with a circumference of the cross-sectional circle of the cylinder to be measured, (ii) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, $L4 = LS4 - \Delta L4$, wherein LS1, LS2, LS3 and LS4 are distances between each of the first, second, third and fourth sensors and the $O_0$, (iii) a step of rotating the cylinder to be measured by $\theta°$ in a direction toward the second sensor from the first sensor, and repeating the steps (i) and (ii), (iv) a step of calculating a distance $\Delta O1$ between a floating point O', which is a point on the cross-sectional circle of the cylinder to be measured corresponding to the $O_0$ before the rotation in the step (iii), and a line passing through the $O_0$ and intersecting at a right-angle with the line connecting the first sensor and the $O_0$, from L1 and L3 obtained in the step (ii) and L2 and L4 obtained in the step (iii), (v) a step of calculating a distance between the O' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (iii) and $\Delta O1$ obtained in the step (iv), and (vi) a step of obtaining the shape of the cross-sectional circle based on the distance calculated in the step (v).

11. A measuring method of a cylindrical shape of a cylinder to be measured by the following steps (I) to (II), comprising:

(I) a step of measuring shapes of a plurality of cross-sectional circles, which are orthogonal to an axis of the cylinder, (II) a step of measuring the cylindrical shape of the cylinder from the shapes of the plurality of cross-sectional circles measured in the step (I), (III) a step of obtaining the shape of the cylinder measured in the step (II), wherein measurements of shapes of the plurality of cross-sectional circles in the step (I), are carried out respectively by the following steps (i) to (viii) using measuring means constructed of (a) a cylinder support jig, and (b) a mount having first, second and third sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the second sensor and the third sensor are θ°, the cross-sectional circle of the reference cylinder being a true circle having a radius of d2, and comprise:

(i) a step of measuring each of distances ΔLR1, ΔLR2 and ΔLR3 between each of the first, second and third sensors and intersecting points of lines connecting the respective sensors and the $O_0$ with a circumference of the cross-sectional circle of the reference cylinder, (ii) a step of calculating each of distances LS1, LS2 and LS3 between each of the first, second and third sensors and the $O_0$ according to the following equations:

$LS1 d2 \Delta LR1$, $LS2 d2 \Delta LR2$, $LS2 d2 \Delta LR3$, (iii) a step of measuring each of distances ΔL1, ΔL2 and ΔL3 between each of the first, second and third sensors and intersecting points of lines connecting the respective sensors and the $O_0$ with a circumference of the cross-sectional circle of the cylinder to be measured.

(iv) a step of calculating each of distances L1, L2 and L3 between the respective intersecting points of lines connecting the respective first, second and third sensors and the $O_0$ with a circumference of a cross-sectional circle of the cylinder to be measured and the $O_0$ according to the following equations:

$L1 = LS1 - L1$, $L2 = LS2 - L2$, $L3 = LS3 - L3$, (v) a step of rotating the cylinder to be measured by θ° in a direction toward the second sensor from the first sensor, and repeating the steps (iii) and (iv), (vi) a step of calculating a distance ΔO1 between a floating point O', which is a point on the cross-sectional circle of the cylinder to be measured corresponding to the $O_0$ before the rotation in the step (v), and a line passing through the $O_0$ and intersecting at a right-angle with the line connecting the first sensor and the $O_0$, from L1 and L2 obtained in the step (iv) and L2 and L3 obtained in the step (v), (vii) a step of calculating a distance between the O' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and ΔO1 obtained in the step (vi), and (viii) a step of obtaining the shape of the cross-sectional circle based on the distance calculated in the step (vii).

12. A measuring method of a cylindrical shape of a cylinder to be measured by the following stens (I) to (III), comprising:

(I) a step of measuring shapes of a plurality of cross-sectional circles, which are orthogonal to an axis of the cylinder, (II) a step of measuring the cylindrical shape of the cylinder from the shapes of the plurality of cross-sectional circles measured in the step (I), (III) a step of obtaining the shape of the cylinder measured in the step (II), wherein measurements of shapes of the plurality of cross-sectional circles in the step (I), are carried out respectively by the following steps (i) to (viii) using measuring means constructed of (a) a cylinder support jig, and (b) a mount having first, second, third and fourth sensors for detecting displacements, which are located on a cross-section including a cross-sectional circle which is orthogonal to an axis of a reference cylinder, are aimed at a measurement reference point ($O_0$) which is an intersecting point of the axis of the reference cylinder with the cross-sectional circle which is orthogonal to the axis of the reference cylinder, and are arranged and fixed so that an angle formed between lines connecting the $O_0$ with the first sensor and the second sensor and an angle formed between lines connecting the $O_0$ with the third sensor and the fourth sensor are θ°, the cross-sectional circle of the reference cylinder being a true circle having a radius of d2, and comprise:

(i) a step of measuring each of distances ΔLR1, ΔLR2, ΔLR3 and ΔLR4 between each of the first, second, third and fourth sensors and intersecting points of lines connecting the respective sensors and the $O_0$ with a circumference of the cross-sectional circle of the reference cylinder, (ii) a step of calculating each of distances LS1, LS2, LS3 and LS4 between each of the first, second, third and fourth sensors and the $O_0$ according to the following equations:

$LS1 = d2 \Delta LR1$, $LS2 = d2 \Delta LR2$, $LS3 = d2 \Delta LR3$, $LS4 = d2 \Delta LR4$, (iii) a step of measuring each of distances ΔL1, ΔL2, ΔL3 and ΔL4 between each of the first, second, third and fourth sensors and intersecting points of lines connecting the respective sensors and the $O_0$ with a circumference of the cross-sectional circle of the cylinder to be measured, (iv) a step of calculating each of distances L1, L2, L3 and L4 between the respective intersecting points of lines connecting the respective first, second, third and fourth sensors and the $O_0$ with a circumference of a cross-sectional circle of the cylinder to be measured and the $O_0$ according to the following equations:

$L1 = LS1 - \Delta L1$, $L2 = LS2 - \Delta L2$, $L3 = LS3 - \Delta L3$, $L4 = LS4 - \Delta L4$, (v) a step of rotating the cylinder to be measured by θ° in a direction toward the second sensor from the first sensor, and repeating the steps (iii) and (iv), (vi) a step of calculating a distance ΔO1 between a floating point O', which is a point on the cross-sectional circle of the cylinder to be measured corresponding to the $O_0$ before the rotation in the step (v), and a line passing through the $O_0$ and intersecting at a right-angle with the line connecting the first sensor and the $O_0$, from L1 and L3 obtained in the step (iv) and L2 and L4 obtained in the sten (v), (vii) a step of calculating a distance between the O' and a line intersecting at a right-angle with a line connecting the first sensor and the $O_0$ at an intersecting point of the line connecting the first sensor and the $O_0$ with a circumference of a cross-sectional circle of the cylinder to be measured after the rotation, from L1 obtained in the step (v) and ΔO1 obtained in the step (vi), and (viii) a step of obtaining the shape of the cross-sectional circle based on the distance calculated in the step (v).

* * * * *

UNITED STATES PATENT AND TRADEMARK OFFICE
CERTIFICATE OF CORRECTION

PATENT NO. : 7,328,125 B2
APPLICATION NO. : 11/469094
DATED : February 5, 2008
INVENTOR(S) : Yasuhiro Kawai et al.

It is certified that error appears in the above-identified patent and that said Letters Patent is hereby corrected as shown below:

COLUMN 3:

Line 49, "$O_0$according" should read --$O_0$ according--.

COLUMN 5:

Line 9, "$\Delta 01$" should read --$\Delta O1$--.

COLUMN 26:

Line 53, "(v)," should read --(vi),--.

COLUMN 27:

Line 56, "(v)," should read --(vi),--.

COLUMN 30:

Line 31, "(vii)." should read --step (vii).--.

COLUMN 31:

Line 55, "(II)" should read --(III)--.
Line 62, "haying" should read --having--.

COLUMN 32:

Line 49, "(II)," should read --(III),--.

UNITED STATES PATENT AND TRADEMARK OFFICE
CERTIFICATE OF CORRECTION

PATENT NO. : 7,328,125 B2
APPLICATION NO. : 11/469094
DATED : February 5, 2008
INVENTOR(S) : Yasuhiro Kawai et al.

It is certified that error appears in the above-identified patent and that said Letters Patent is hereby corrected as shown below:

COLUMN 33:

Lines 23-27, "$LS1d2\Delta LR1,$            --$LS1=d2+\Delta LR1,$
             $LS2d2\Delta LR2,$  should read  $LS2=d2+\Delta LR2,$
             $LS2d2\Delta LR3,$"           $LS2=d2+\Delta LR3,$--.
Lines 40-44, "$L1=LS1-L1,$             --$L1=LS1-\Delta L1,$
             $L2=LS2-L2,$  should read  $L2=LS2-\Delta L2,$
             $L3=LS3-L3,$             $L3=LS3-\Delta L3,$--.
Line 47, "$\theta^0 in$" should read --$\theta^0$ in--.

COLUMN 34:

Line 2, "stens" should read --steps--.
Lines 41-47, "$LS1=d2\Delta LR1,$            --$LS1=d2+\Delta LR1,$
             $LS2=d2\Delta LR2,$  should read  $LS2=d2+\Delta LR2,$
             $LS3=d2\Delta LR3,$             $LS3=d2+\Delta LR3,$
             $LS4=d2\Delta LR4,$"           $LS4=d2+\Delta LR4$--.

COLUMN 35:

Line 11, "sten (v)," should read --step (v),--.

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,328,125 B2
APPLICATION NO.   : 11/469094
DATED             : February 5, 2008
INVENTOR(S)       : Kawai et al.

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 51 days Delete the phrase "by 51 days" and insert -- by 45 days --

Signed and Sealed this

Eighteenth Day of August, 2009

David J. Kappos
*Director of the United States Patent and Trademark Office*